(12) United States Patent
Greenberg et al.

(10) Patent No.: US 8,239,034 B2
(45) Date of Patent: Aug. 7, 2012

(54) VISUAL PROSTHESIS

(75) Inventors: Robert J. Greenberg, Los Angeles, CA (US); Mark S. Humayun, Glendale, CA (US); Kelly H. McClure, Simi Valley, CA (US); Matthew J. McMahon, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 11/875,760

(22) Filed: Oct. 19, 2007

(65) Prior Publication Data

US 2008/0262571 A1    Oct. 23, 2008

Related U.S. Application Data

(60) Provisional application No. 60/853,477, filed on Oct. 20, 2006.

(51) Int. Cl.
*A61N 1/18* (2006.01)
(52) U.S. Cl. ......................................................... 607/54
(58) Field of Classification Search ...................... 607/54
See application file for complete search history.

(56) References Cited

U.S. PATENT DOCUMENTS

| 4,573,481 | A |  | 3/1986 | Bullara |  |
|---|---|---|---|---|---|
| 4,628,933 | A |  | 12/1986 | Michelson |  |
| 4,837,049 | A |  | 6/1989 | Byers et al. |  |
| 5,109,844 | A |  | 5/1992 | de Juan, Jr. et al. |  |
| 5,215,088 | A |  | 6/1993 | Normann et al. |  |
| 5,341,807 | A | * | 8/1994 | Nardella | 600/381 |
| 5,935,155 | A |  | 8/1999 | Humayun et al. |  |
| 6,393,327 | B1 |  | 5/2002 | Scribner |  |
| 6,400,989 | B1 |  | 6/2002 | Eckmiller |  |
| 6,458,157 | B1 |  | 10/2002 | Suaning |  |
| 6,714,806 | B2 | * | 3/2004 | Iaizzo et al. | 600/374 |
| 7,177,690 | B2 | * | 2/2007 | Woods et al. | 607/29 |
| 2003/0199938 | A1 | * | 10/2003 | Smits et al. | 607/27 |
| 2006/0129207 | A1 |  | 6/2006 | Fried et al. |  |
| 2006/0241721 | A1 | * | 10/2006 | Kothandaraman et al. | 607/46 |
| 2006/0247754 | A1 |  | 11/2006 | Greenberg et al. |  |

OTHER PUBLICATIONS

Humayun, M.S. Intraocular Retinal Prosthesis. Trans Am Ophthalmol Soc. 2001; 99: 271-300.*
Mahadevappa et al. Perceptual Thresholds and Electrode Impedance in Three Retinal Prosthesis Subjects. IEEE Transactions on Neural Systems and Rehabilitation Engineering. Jun. 2005; 13,2: 201-206.*

* cited by examiner

*Primary Examiner* — Carl H Layno
*Assistant Examiner* — Jeremiah Kimball
(74) *Attorney, Agent, or Firm* — Scott B. Dunbar; Alessandro Steinfl

(57) ABSTRACT

A method to provide visual current feedback of a retinal stimulation system. The method comprising: providing a retinal stimulation system configured to stimulate neural tissue in a subject's eye, the retinal stimulation system comprising: an electronics package; and at least a first and a second electrode, each associated with the electronics package and configured to apply current to a subject's retina; wherein current to be applied by the first electrode and the second electrode is configured to be higher for the first electrode when the first electrode has an impedance lower than a second electrode's impedance; and providing a visual interface configured to show impedance of at least one of the electrodes.

8 Claims, 21 Drawing Sheets

VISUAL PROSTHESIS

CROSS REFERENCE TO RELATED APPLICATIONS

This application claims the benefit of U.S. provisional Patent Application Ser. No. 60/853,477, filed Oct. 20, 2006 for "Real Time Electrode Impedance Measurement and Data Display for an Implantable Device" by Robert J. Greenberg, Mark S. Humayun, Kelly H. McClure and Matthew J. McMahon, the disclosure of which is incorporated herein by reference.

FEDERALLY SPONSORED RESEARCH OR DEVELOPMENT

The present invention was made with support from the United States Government under Grant number R24EY12893-01, awarded by the National Institutes of Health. The United States Government has certain rights in the invention.

FIELD

The present disclosure relates to visual prostheses configured to provide neutral stimulation for the creation of artificial vision.

BACKGROUND

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat.

No. 5,935,155 to Humayun describes a visual prosthesis for use with the flat retinal array described in de Juan.

SUMMARY

According to a first aspect, a method for stimulating a subject's retina is disclosed, the method comprising: selecting at least a first and a second electrode each configured to apply current to a subject's retina; determining impedance for the at least first electrode and second electrode; and applying current to the subject's retina through the at least first and second electrode, wherein current to be applied by the first electrode and the second electrode is configured to be higher for the first electrode when the first electrode has an impedance lower than a second electrode's impedance.

According to a second aspect, a method for implanting electrodes in a subject's retina is disclosed, the method comprising: a) temporarily placing electrodes in a subject's retina; b) determining impedance of the placed electrodes; and c) repeating features a) and b) until impedance of the electrodes is ideal for permanent implanting of the electrodes.

According to a third aspect, a method for applying current to a load is disclosed, the method comprising selecting a first and a second electrode each configured to apply current to a load; determining impedance of the electrodes; and applying current to the load through the first and second electrode, wherein current to be applied by the first electrode and the second electrode is configured to be higher for the first electrode when the first electrode has an impedance lower than a second electrode's impedance.

According to a fourth aspect, a method for stimulating a subject's retina is disclosed, the method comprising selecting at least a first and a second electrode, each configured to apply current to a subject's retina; and applying current to the subject's retina through the first and second electrode, wherein current to be applied by the first electrode and the second electrode is configured to be higher for the first electrode when the first electrode is disposed farther from the subject's retina than the second electrode.

According to a fifth aspect, a method for determining which electrode is to be in contact with a subject's retina is disclosed, the method comprising: applying current to a plurality of electrodes implanted in the subject's eye; and determining impedance of each electrode of the plurality of electrodes, establishing the electrode with the highest impedance as the electrode in contact with the subject's retina.

According to a sixth aspect, a method to provide visual current feedback of a retinal stimulation system is disclosed, the method comprising: providing a retinal stimulation system configured to stimulate neural tissue in a subject's eye, the retinal stimulation system comprising: an electronics package; and at least a first and a second electrode, each associated with the electronics package and configured to apply current to a subject's retina; wherein current to be applied by the first electrode and the second electrode is configured to be higher for the first electrode when the first electrode has an impedance lower than a second electrode's impedance; and providing a visual interface configured to show impedance of at least one of the electrodes.

According to a seventh aspect, a method for providing visual current feedback when implanting electrodes in a subject's retina, is disclosed, the method comprising: a) temporarily placing electrodes in a subject's retina; b) determining impedance of the placed electrodes; c) monitoring impedance of at least one of the electrodes using a visual interface; d) repeating features a) and c) until impedance of the electrodes is ideal for permanent implanting of the electrodes.

According to an eight aspect, a computer-operated system comprising a display component, the display component having a graphical user interface associated with the method for implanting electrodes in a subject's retina is disclosed, the method comprising: a) placing electrodes in a subject's retina; b) determining impedance of the placed electrodes; c) repeating features a) and b) until impedance of the electrodes is ideal for implanting of the electrodes; and the graphical user interface comprising: a diagnostic module screen; and a measure impedance button.

According to a ninth aspect, a computer implemented method for testing impedance of electrodes is disclosed, the method comprising: a) setting a counter to an initial value; b) incrementing the value of the counter; c) stimulating an electrode that corresponds to the value of the counter; d) measuring a voltage drop across the stimulated electrode; and e) repeating features b) through d) until the value of the counter reflects the total number of electrodes being tested.

According to a tenth aspect, a method to provide visual current feedback when determining which electrode is to be in contact with a subject's retina is disclosed, the method comprising: applying current to a plurality of electrodes implanted in the subject's eye; determining impedance of each electrode of the plurality of electrodes; providing a visual interface configured to show impedance of at least one of the electrodes; and establishing the electrode with the highest impedance as the electrode in contact with the subject's retina.

According to an eleventh aspect, a retinal stimulation system configured to stimulate neural tissue in a subject's eye is disclosed, the retinal stimulation system comprising: an electronics package; and at least a first and a second electrode, each associated with the electronics package and configured to apply current to a subject's retina; wherein current to be applied by the first electrode and the second electrode is configured to be higher for the first electrode when the first electrode has an impedance lower than a second electrode's impedance.

According to a twelfth aspect, a device configured to apply current to a load is disclosed, the device comprising: a current source; and at least a first and a second electrode each associated with the current source and configured to apply current to a load; wherein current to be applied by the first electrode and the second electrode is configured to be higher for the first electrode when the first electrode has an impedance lower than a second electrode's impedance.

According to a thirteenth aspect, a retinal stimulation system configured to stimulate retina's neural tissue in a subject's eye is disclosed, the retinal stimulation system comprising: an electronics package; and at least a first and a second electrode each associated with the electronics package and configured to apply current to a subject's retina; wherein current to be applied by the first electrode and the second electrode is configured to be higher for the first electrode when the first electrode is disposed farther from a retina than the second electrode.

Further embodiments are shown in the specification, drawings and claims of the present application.

BRIEF DESCRIPTION OF THE FIGURES

FIGS. 13-1, 13-2, 13-3 and 13-4 show an exemplary embodiment of a video processing unit. FIG. 13-1 should be viewed at the left of FIG. 13-2. FIG. 13-3 should be viewed at the left of FIG. 13-4. FIGS. 13-1 and 13-2 should be viewed on top of FIGS. 13-3 and 13-4.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure is concerned with a visual apparatus and a method for creation of artificial vision. In particular, the present disclosure provides an interface and method for controlling a visual prosthesis (i.e. device) implanted in an individual patient (i.e. subject) to create artificial vision.

Figure 1:
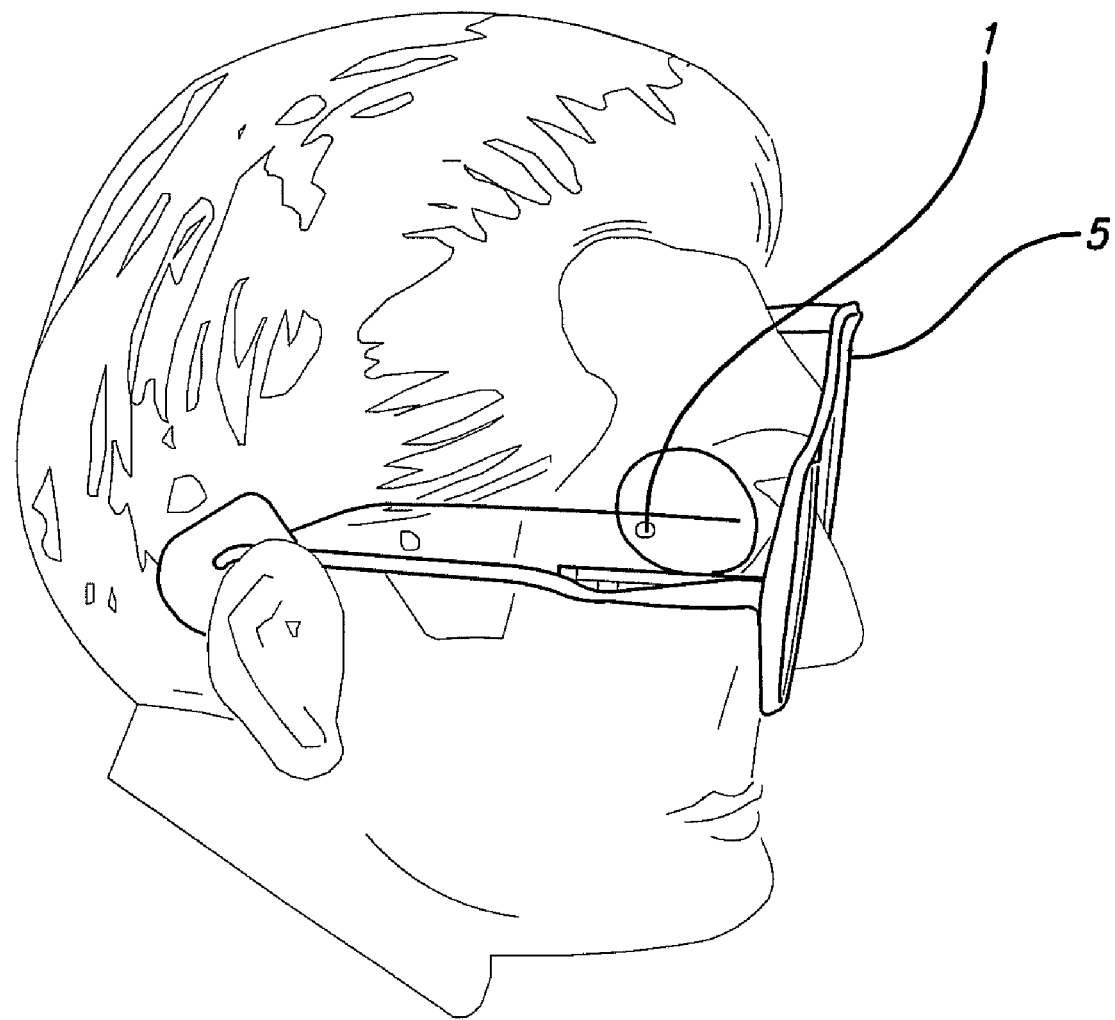
FIG. 1 shows a visual prosthesis apparatus according to the present disclosure.

FIG. 1 shows a visual prosthesis apparatus. The visual apparatus comprises, in combination, an implantable retinal stimulation system 1 and a video capture/transmission apparatus or visor embodied in visor/Glasses 5. An exemplary retinal stimulation system 1 is shown in more detail in FIGS. 2-5 and an exemplary visor 5 is shown in more detail in FIGS. 6 and 7.

The retinal stimulation system 1 is further disclosed in U.S. application Ser. No. 11/207,644, filed Aug. 19, 2005 for "Flexible Circuit Electrode Array" by Robert J. Greenberg, et. al. incorporated herein by reference, and is intended for use in subjects with retinitis pigmentosa. The visor 5 is further disclosed in International Patent Application No. PCT/US07/13918, filed on Jun. 14, 2007 and entitled "APPARATUS AND METHOD FOR ELECTRICAL STIMULATION OF HUMAN RETINA," also incorporated herein by reference.

Figure 2:
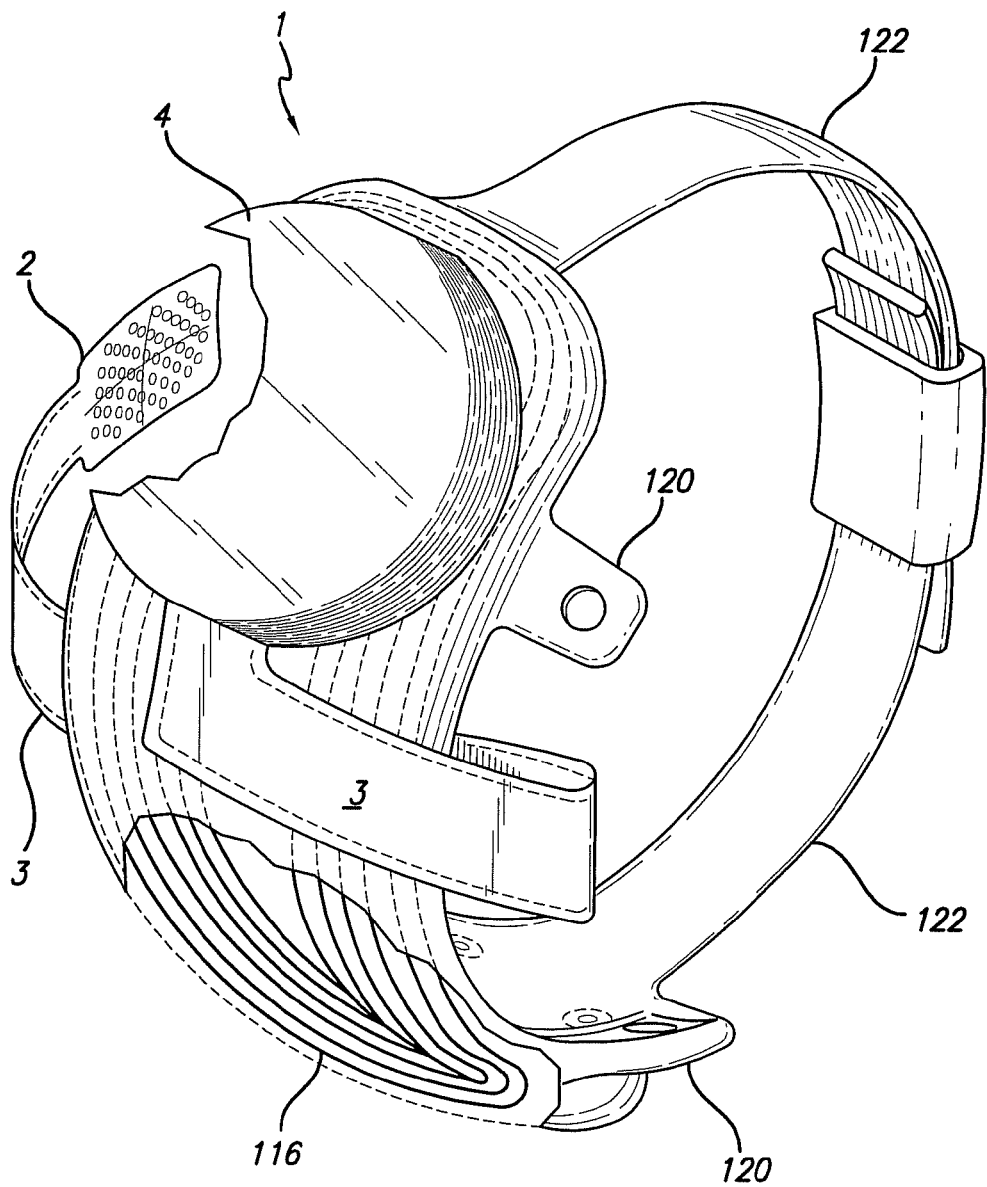
FIGS. 2 and 3 show a retinal stimulation system adapted to be implanted into a subject.
Figure 3:
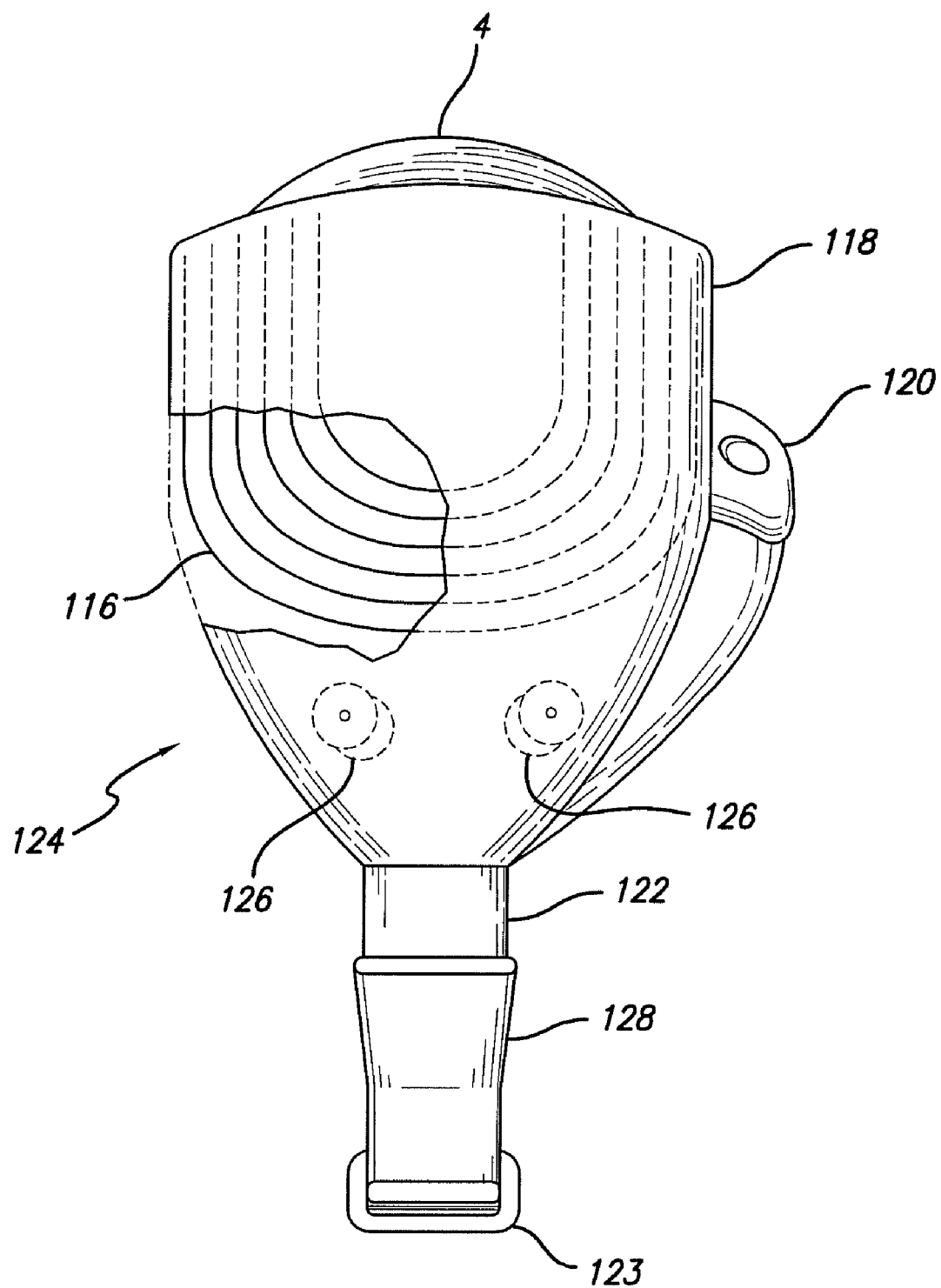

The exemplary retinal stimulation system 1, shown in FIGS. 2 and 3, is an implantable electronic device containing an inductive coil 116 and an electrode array 2 that is electrically coupled by a cable 3 that pierces sclera of the subject's eye to an electronics package 4, external to the sclera. The retinal stimulation system 1 is designed, for example, to elicit visual percepts in blind subjects with retinitis pigmentosa.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 2 that is wider than it is tall. This is equally applicable to a cortical visual array. In which case, the wider dimension is not horizontal on the visual cortex, but corresponds to horizontal in the visual scene.

Figure 8:
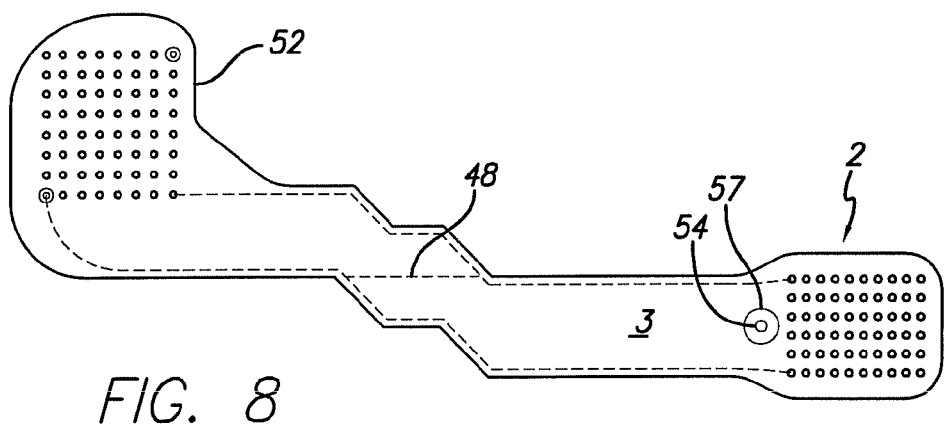
FIG. 8 shows a flexible circuit electrode array, also shown in FIG. 2.

FIG. 8 shows the flexible circuit electrode array 2 prior to folding and attaching to the electronics package 4 of FIG. 2. At one end of the flexible circuit cable 3 is an interconnection pad 52 for connection to the electronics package 4. At the other end of the flexible circuit cable 3 is the flexible circuit electrode array 2. Further, an attachment point 54 may be provided near the flexible circuit electrode array 2. A retina tack (not shown) is placed through the attachment point 54 to hold the flexible circuit electrode array 2 to the retina. A stress relief 57 may be provided surrounding the attachment point 54. The stress relief 57 may be made of a softer polymer than the flexible circuit, or it may include cutouts or thinning of the polymer to reduce the stress transmitted from the retina tack to the flexible circuit electrode array 2. The flexible circuit cable 3 may be formed in a dog leg pattern so than when it is folded at fold 48 it effectively forms a straight flexible circuit cable 3 with a narrower portion at the fold 48 for passing through the sclerotomy. The electrode array 2 may comprise a polyimide cable that houses wire conductors and an array of exposed platinum electrodes in a grid. In one embodiment, there are sixty electrodes arranged in a 6×10 grid.

The electronics package 4 of FIGS. 2 and 3 can be electrically coupled to the inductive coil 116. In one aspect, the inductive coil 116 contains a receiver and transmitter antennae made from wound wire. Alternatively, the inductive coil 116 may be made from a thin film polymer sandwich with wire traces deposited between layers of thin film polymer. The electronics package 4 may contain components and an Application Specific Integrated Circuit (ASIC) for processing the received data and using the received power to generate the required stimulation output. The electronics package 4 and the inductive coil 116 may be held together by a molded body 118 shown in FIG. 3. As also shown in FIG. 3, the molded body 118 may also include suture tabs 120 shown in FIG. 3. The molded body narrows to form a strap 122 which surrounds the sclera and holds the molded body 118, inductive coil 116, and electronics package 4 in place. The molded body 118, suture tabs 120 and strap 122 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the inductive coil 116 and molded body 118 are oval shaped, and in this way, a strap 122 can better support the oval shaped coil.

The eye moves constantly. The eye moves to scan a scene and also has a jitter motion to prevent image stabilization. Even though such motion is useless in the blind, it often continues long after a person has lost their sight. Thus, in one embodiment of the present disclosure, the entire retinal stimulation system 1 of the prosthesis is attached to and supported by the sclera of a subject. By placing the device under the rectus muscles with the electronics package in an area of fatty tissue between the rectus muscles, eye motion does not cause any flexing which might fatigue, and eventually damage, the device.

FIG. 3 shows a side view of the retinal stimulation system 1, in particular, emphasizing the fan tail 124. When the retinal prosthesis is implanted, the strap 122 is passed under the eye muscles to surround the sclera. The inductive coil 116 and molded body 118 should also follow the strap under the lateral rectus muscle on the side of the sclera. The retinal stimulation system 1 of the visual prosthesis apparatus is very delicate. It is easy to tear the molded body 118 or break wires in the inductive coil 116. In order to allow the molded body 118 to slide smoothly under the lateral rectus muscle, the molded body is shaped in the form of a fan tail 124 on the end opposite the electronics package 4. Element 123 shows a retention sleeve, while elements 126 and 128 show holes for surgical positioning and a ramp for surgical positioning, respectively.

Figure 4:
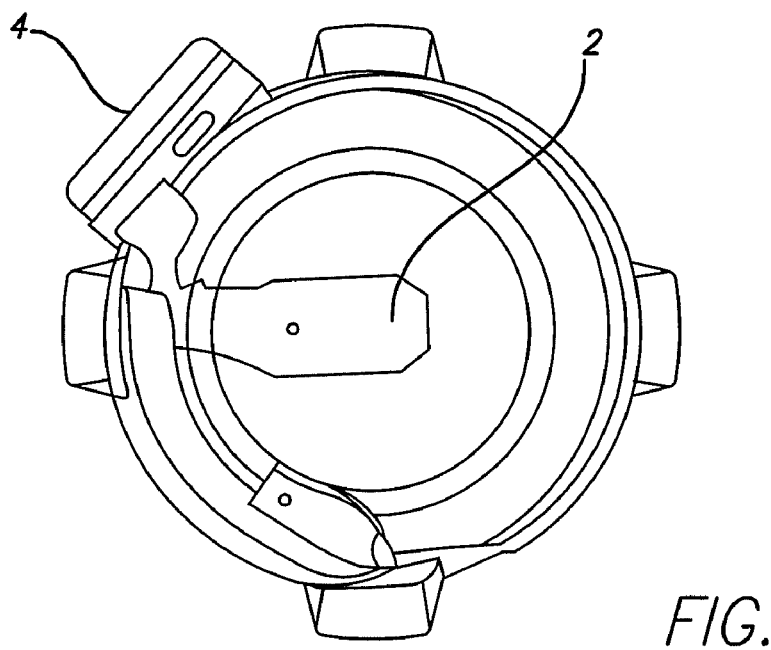
FIG. 4 shows a front view of the implanted retinal stimulation system.
Figure 5:
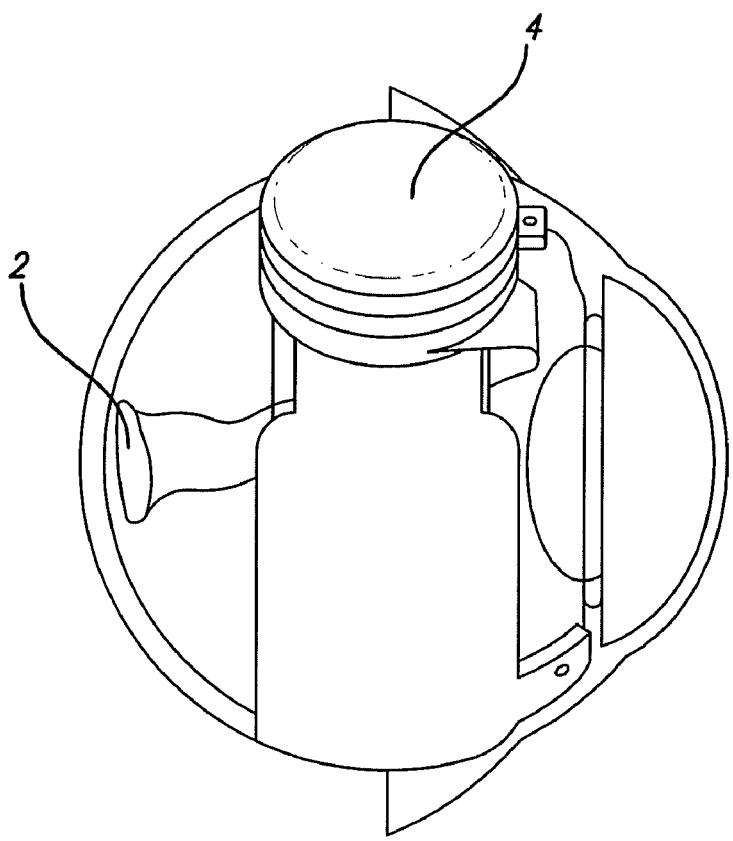
FIG. 5 shows a side view of the implanted system of FIG. 9.

FIGS. 4 and 5 show front and side views of the Retinal stimulation system 1 implanted with respect to the subject's eye 7. As shown in FIGS. 4 and 5, the electrode array 2 enters the eye through a pars plana incision and is placed on the retina over the fovea using a retinal tack. The remaining Retinal stimulation system 1 is secured to the eye by means of a scleral band held in place by a Watzke sleeve (typical of scleral procedures), and also by suture tabs. Additionally, another suture may be placed around the scleral band in the inferior medical quadrant of the eye.

Figure 6:
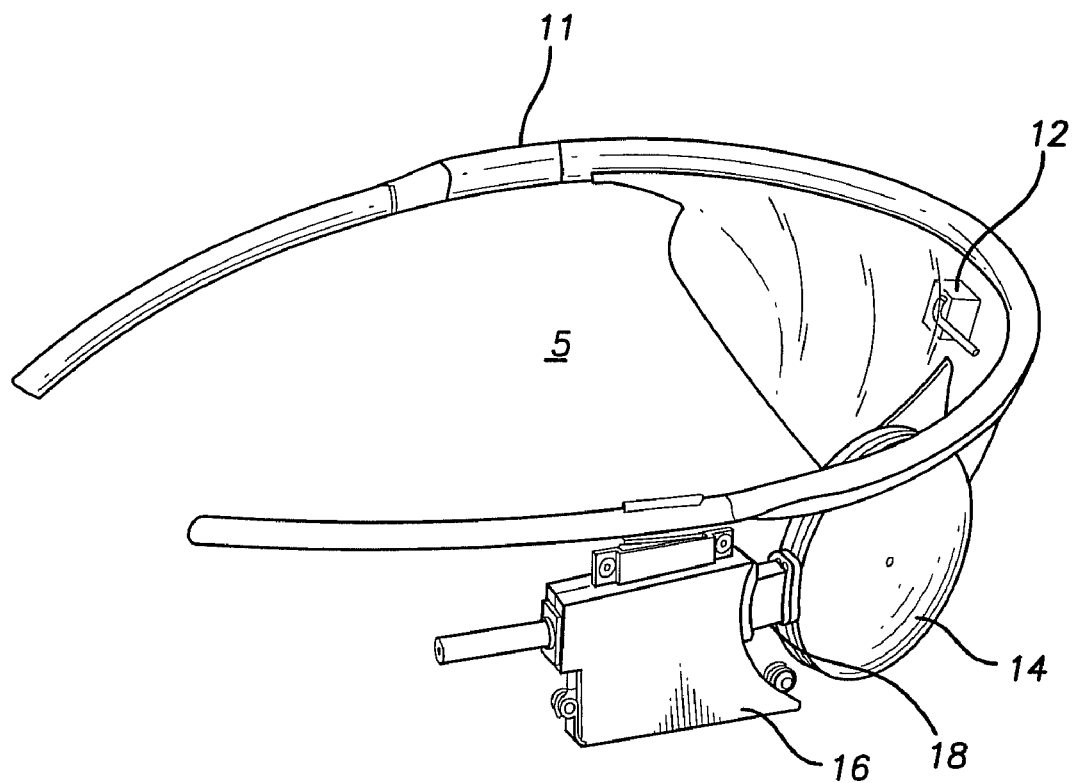
FIGS. 6 and 7 show a video capture/transmission apparatus or visor adapted to be used in combination with the retinal stimulation system of FIGS. 2-5.
Figure 7:
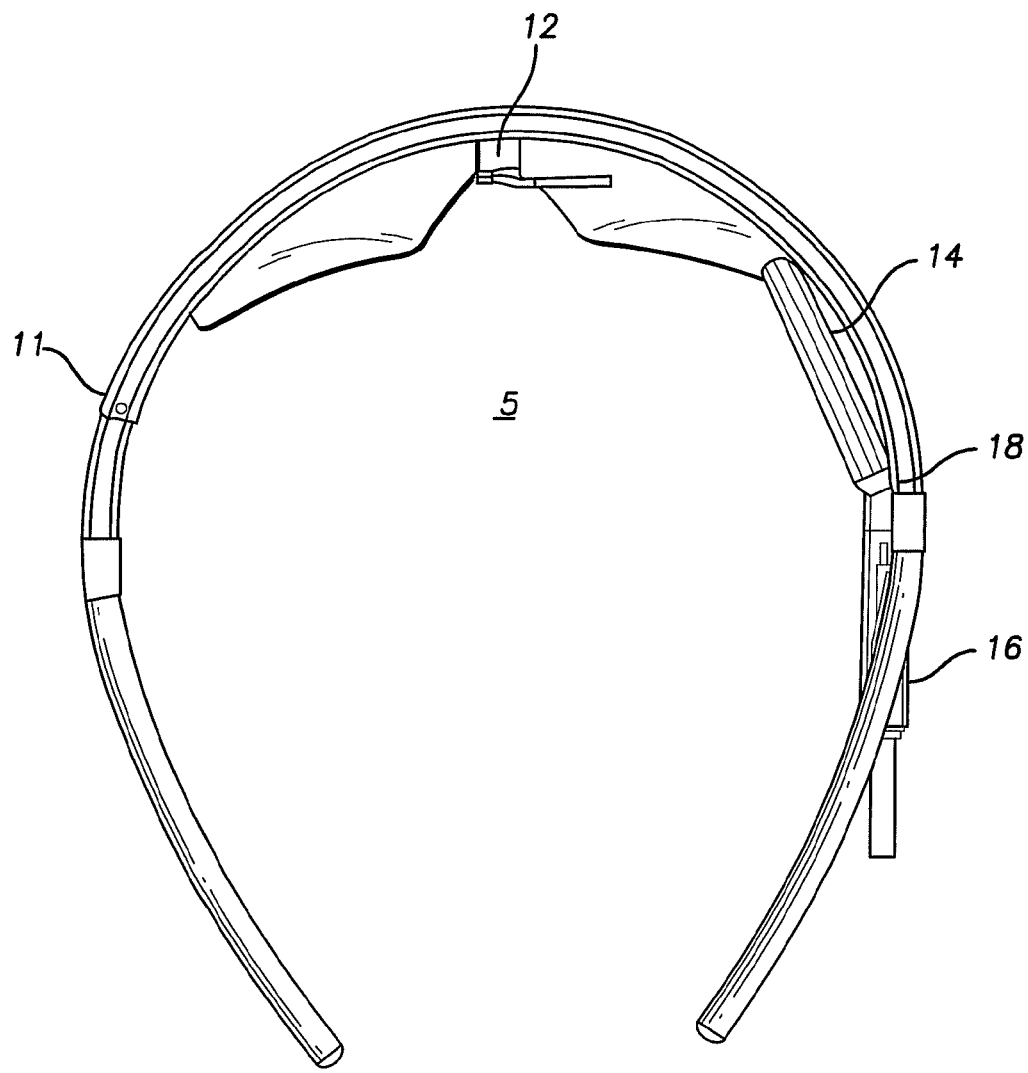

Referring to FIGS. 6 and 7, the glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIGS. 9-12 and discussed below), which processes the video signal and subsequently transforms the processed video signal into electrical stimulation patterns or data. The electrical stimulation data are then sent to the external coil 14 that sends both data and power via radio-frequency (RF) telemetry to the coil 116 of the retinal stimulation system 1, shown in FIGS. 2 and 3. The coil 116 receives the RF commands which control the application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2 (shown in FIGS. 2, 3 and 8). In one exemplary embodiment, the electrical stimulation patterns or data being transmitted by the external coil 14 is binary data. The external coil 14 may contain a receiver and transmitter antennae and a radio-frequency (RF) electronics card for communicating with the internal coil 116.

Figure 9:
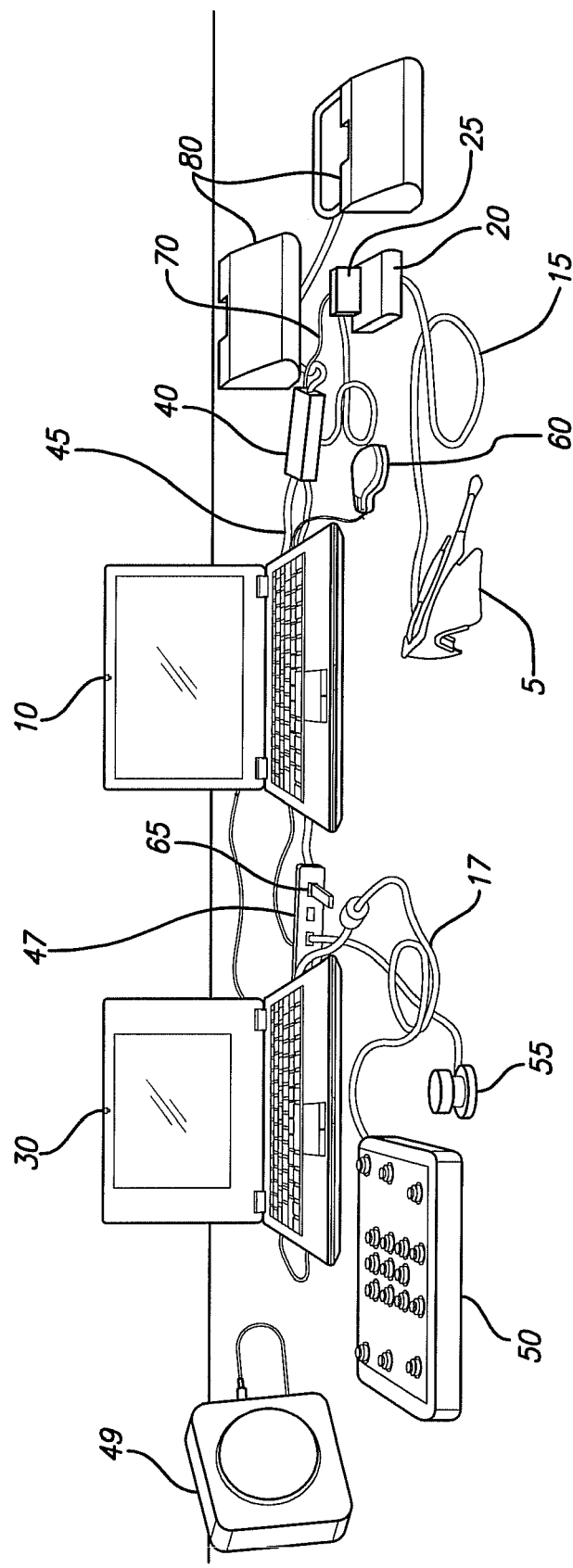
FIG. 9 shows components of a fitting system according to the present disclosure, the system also comprising the visor shown in FIGS. 6-7.

Referring to FIG. 9, a Fitting System (FS) may be used to configure and optimize the visual prosthesis apparatus shown in FIG. 1. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to nm psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 10 of FIG. 9 may be connected to the VPU 20 using an optically isolated serial connection adapter 40. Because it is optically isolated, the serial connection adapter 40 assures that no electric leakage current can flow from the Fitting System laptop 10 in the even of a fault condition.

As shown in FIG. 9, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

In one exemplary embodiment, the Fitting System shown in FIG. 9 may be used to configure system stimulation parameters and video processing strategies for each subject outfitted with the visual prosthesis apparatus of FIG. 1. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system 1. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 7 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-tempral electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

Figure 10:
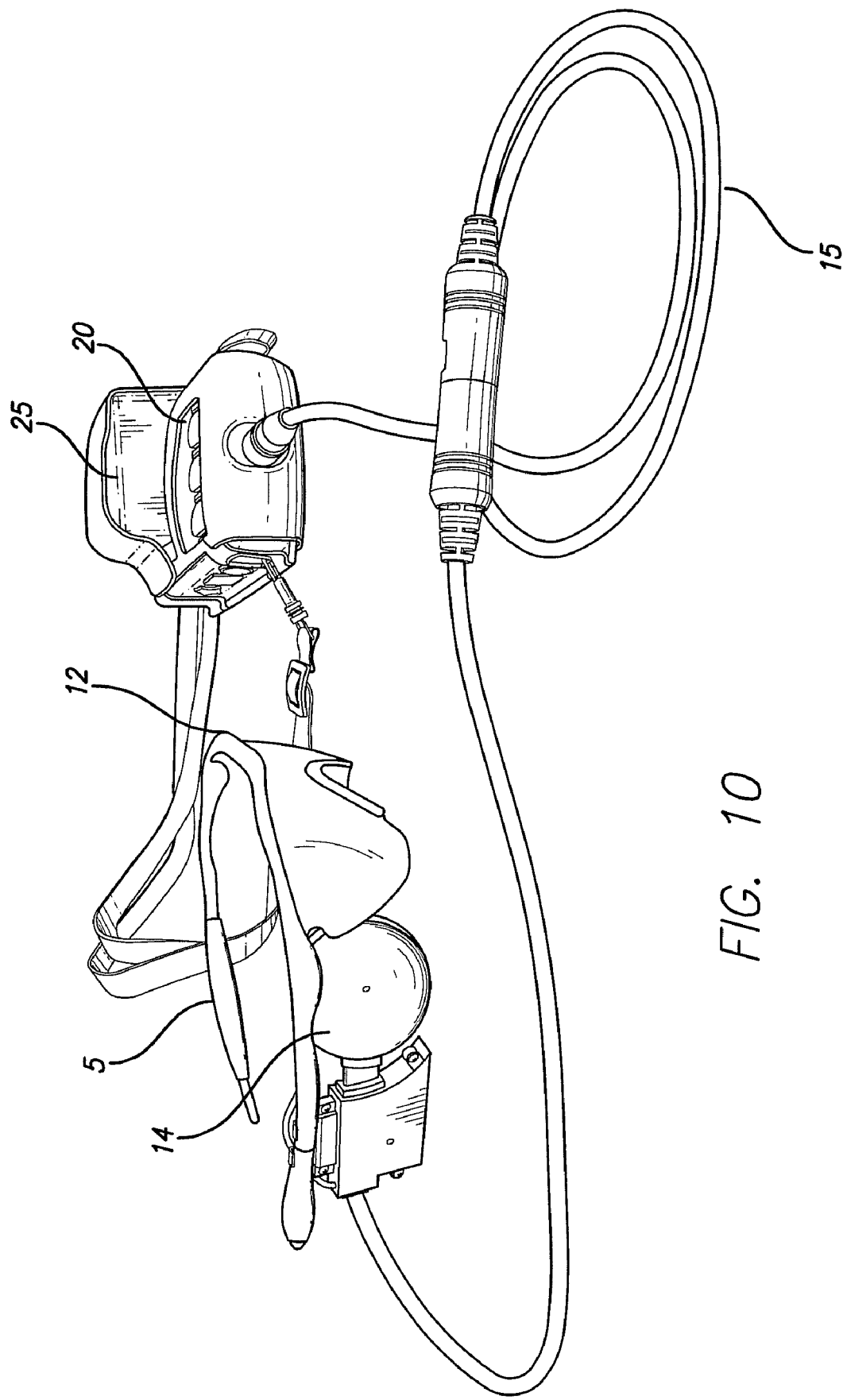
FIG. 10 shows the visual prosthesis apparatus in a stand-alone mode, i.e. comprising the visor of FIGS. 6-7 connected to a video processing unit.

The visual prosthesis apparatus of FIG. 1 may operate in two modes: i) stand-alone mode and ii) communication mode Stand-Alone Mode Referring to FIGS. 1, 2 and 10, in the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system 1 (FIGS. 2 and 3). The internal coil 116 of the retinal stimulation system 1 receives the RF commands from the external coil 14 and transmits them to the electronics package 4 that in turn delivers stimulation to the retina via the electrode array 2. Additionally, the retinal stimulation system 1 may communicate safety and operational status back to the VPU 20 by transmitting RF telemetry from the internal coil 116 to the external coil 14. The visual prosthesis apparatus of FIG. 1 may be configured to electrically activate the retinal stimulation system 1 only when it is powered by the VPU 20 through the external coil 14. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system 1 as is done for example in the stand-alone mode described above. Referring to FIG. 9, in the communication mode, the VPU 20 is connected to the Fitting System laptop 10 using cables 70, 45 and the optically isolated serial connection adapter 40. In this mode, laptop 10 generated stimuli may be presented to the subject and programming parameters may be adjusted and downloaded to the VPU 20. The Psychophysical Test System (PTS) laptop 30 connected to the Fitting System laptop 10 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system 1 can also be tested pre-operatively and intra-operatively (i.e. before operation and during operation) by using an external coil 14, without the glasses 5, placed in close proximity to the retinal stimulation system 1. The coil 14 may communicate the status of the retinal stimulation system 1 to the VPU 20 that is connected to the Fitting System laptop 10 as shown in FIG. 9.

As discussed above, the VPU 20 processes the image from the camera 12 and transforms the image into electrical stimulation patterns for the retinal stimulation system 1. Filters such as edge detection filters may be applied to the electrical stimulation patterns for example by the VPU 20 to generate, for example, a stimulation pattern based on filtered video data that the VPU 20 turns into stimulation data for the retinal stimulation system 1. The images may then be reduced in resolution using a downscaling filter. In one exemplary embodiment, the resolution of the image may be reduced to match the number of electrodes in the electrode array 2 of the retinal stimulation system 1. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system 1 in frames that may employ a cyclic redundancy check (CRC) error detection scheme.

Figure 11:
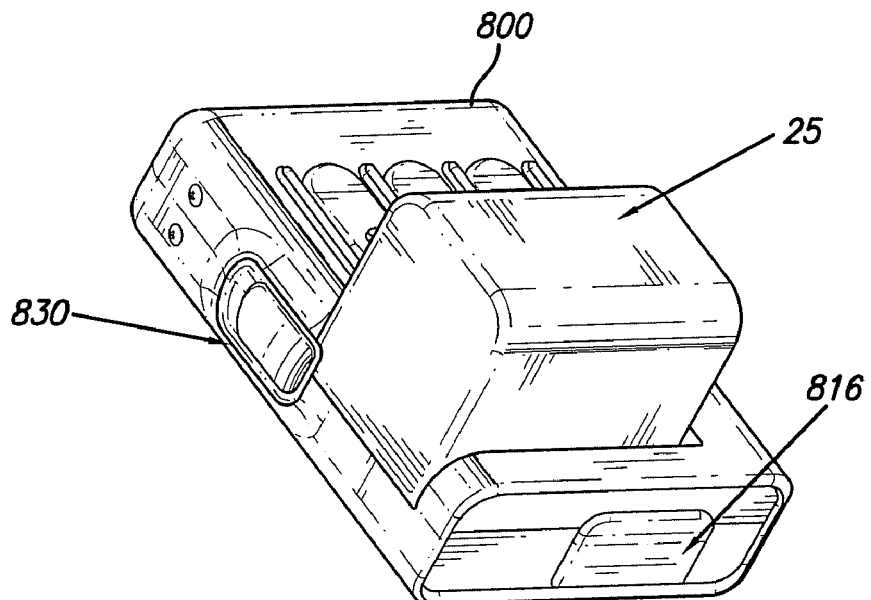
FIGS. 11-12 show the video processing unit already briefly shown with reference to FIGS. 9-10.
Figure 12:
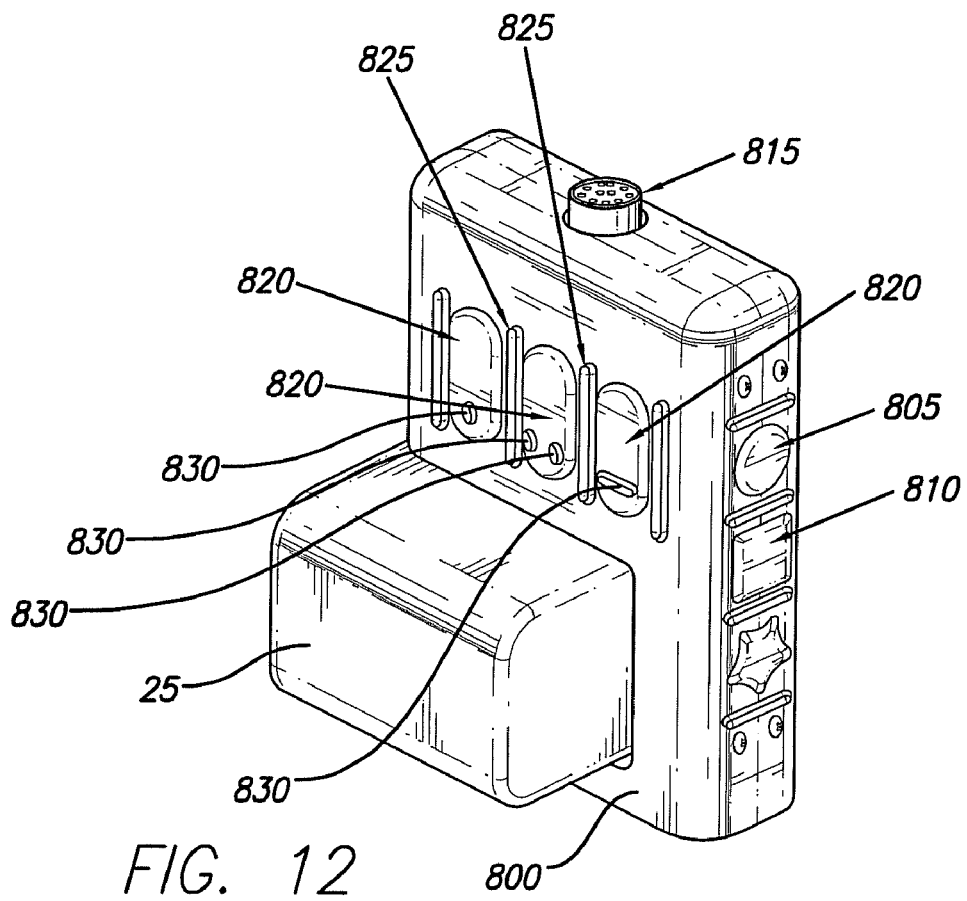

In one exemplary embodiment, the VPU 20 may be configured to allow the subject/patient i) to turn the visual prosthesis apparatus on and off, ii) to manually adjust settings, and iii) to provide power and data to the retinal stimulation system 1. Referring to FIGS. 11 and 12, the VPU 20 may comprise a case 800, power button 805 for turning the VPU 20 on and off, setting button 810, zoom buttons 820 for controlling the camera 12, connector port 815 for connecting to the Glasses 5, a connector port 816 for connecting to the laptop 10 through the connection adapter 40, indicator lights 825 to give visual indication of operating status of the system, the rechargeable battery 25 for powering the VPU 20, battery latch 830 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 12 to help the user identify the functionality of the button without having to look at it. As shown in FIG. 12, the power button 805 may be a circular shape while the settings button 820 may be square shape and the zoom buttons 820 may have special raised markings 830 to also identify each buttons functionality. One skilled in the art would appreciate that other shapes and markings can be used to identify the buttons without departing from the spirit and scope of the invention. For example, the markings can be recessed instead of raised.

In one embodiment, the indicator lights 825 may indicate that the VPU 20 is going through system start-up diagnostic testing when the one or more indicator lights 825 are blinking fast (more then once per second) and are green in color. The indicator lights 825 may indicate that the VPU 20 is operating normally when the one or more indicator lights 825 are blinking once per second and are green in color. The indicator lights 825 may indicate that the retinal stimulation system 1 has a problem that was detected by the VPU 20 at start-up diagnostic when the one or more indicator lights 825 are blinking for example once per five second and are green in color. The indicator lights 825 may indicate that the video signal from camera 12 is not being received by the VPU 20 when the one or more indicator lights 825 are always on and are amber color. The indicator lights 825 may indicate that there is a loss of communication between the retinal stimulation system 1 and the external coil 14 due to the movement or removal of Glasses 5 while the system is operational or if the VPU 20 detects a problem with the retinal stimulation system 1 and shuts off power to the retinal stimulation system 1 when the one or more indicator lights 825 are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As would be clear to one skilled in the are different periodic beeping may also be used to indicate a low battery voltage warning, that there is a problem with the video signal, and/or there is a loss of communication between the retinal stimulation system 1 and the external coil 14. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 20 is in constant communication with the retinal stimulation system 1 through forward and backward telemetry. In this document, the forward telemetry refers to transmission from VPU 20 to the retinal stimulation system 1 and the backward telemetry refers to transmissions from the Retinal stimulation system 1 to the VPU 20. During the initial setup, the VPU 20 may transmit null frames (containing no stimulation information) until the VPU 20 synchronizes with the Retinal stimulation system 1 via the back telemetry. In one embodiment, an audio alarm may be used to indicate whenever the synchronization has been lost.

In order to supply power and data to the Retinal stimulation system 1, the VPU 20 may drive the external coil 14 with a 3 MHz signal. To protect the subject, the retinal stimulation system 1 may comprise a failure detection circuit to detect direct current leakage and to notify the VPU 20 through back telemetry so that the visual prosthesis apparatus can be shut down.

Figures 1, 13:
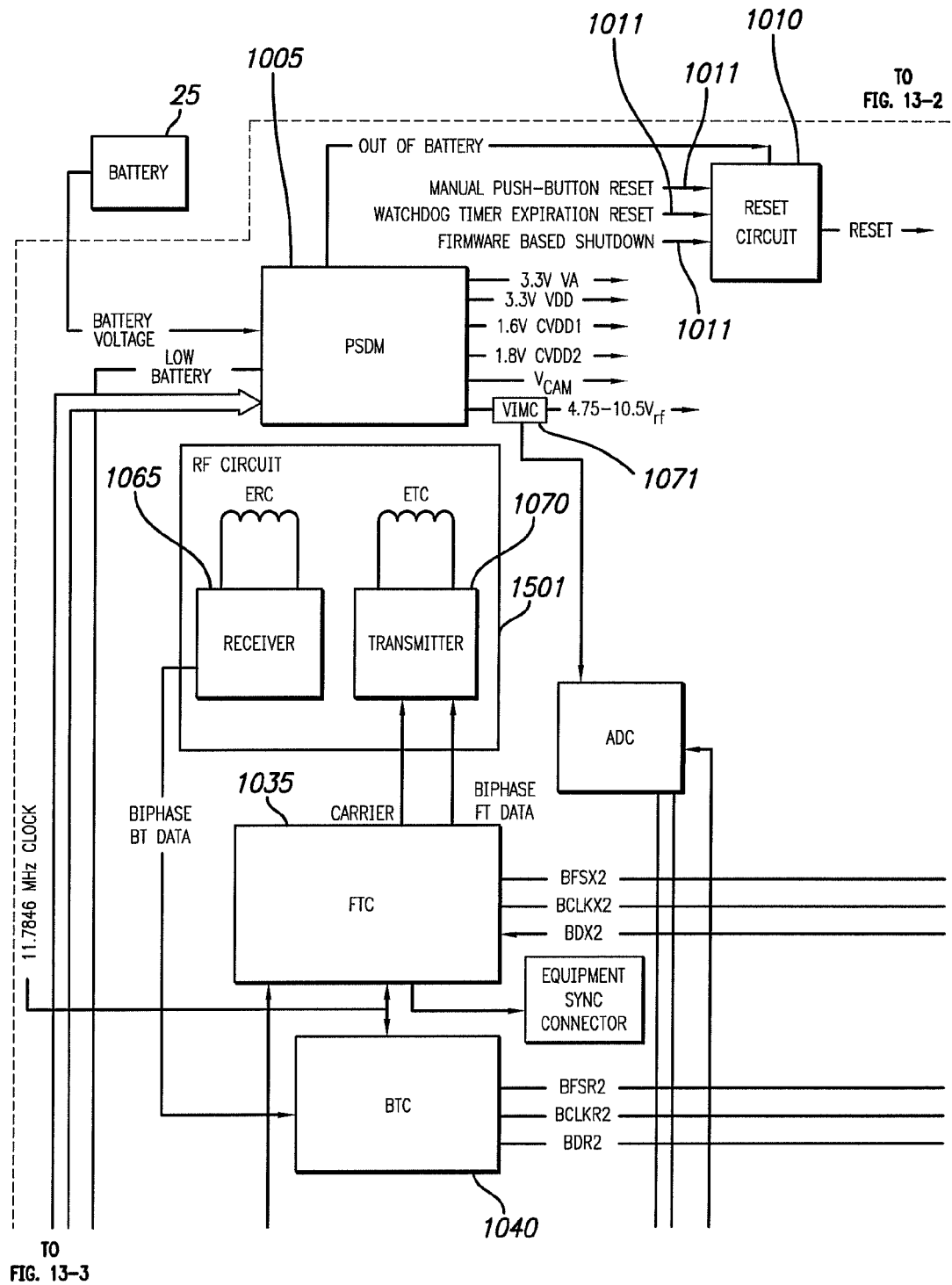
Figures 2, 13:
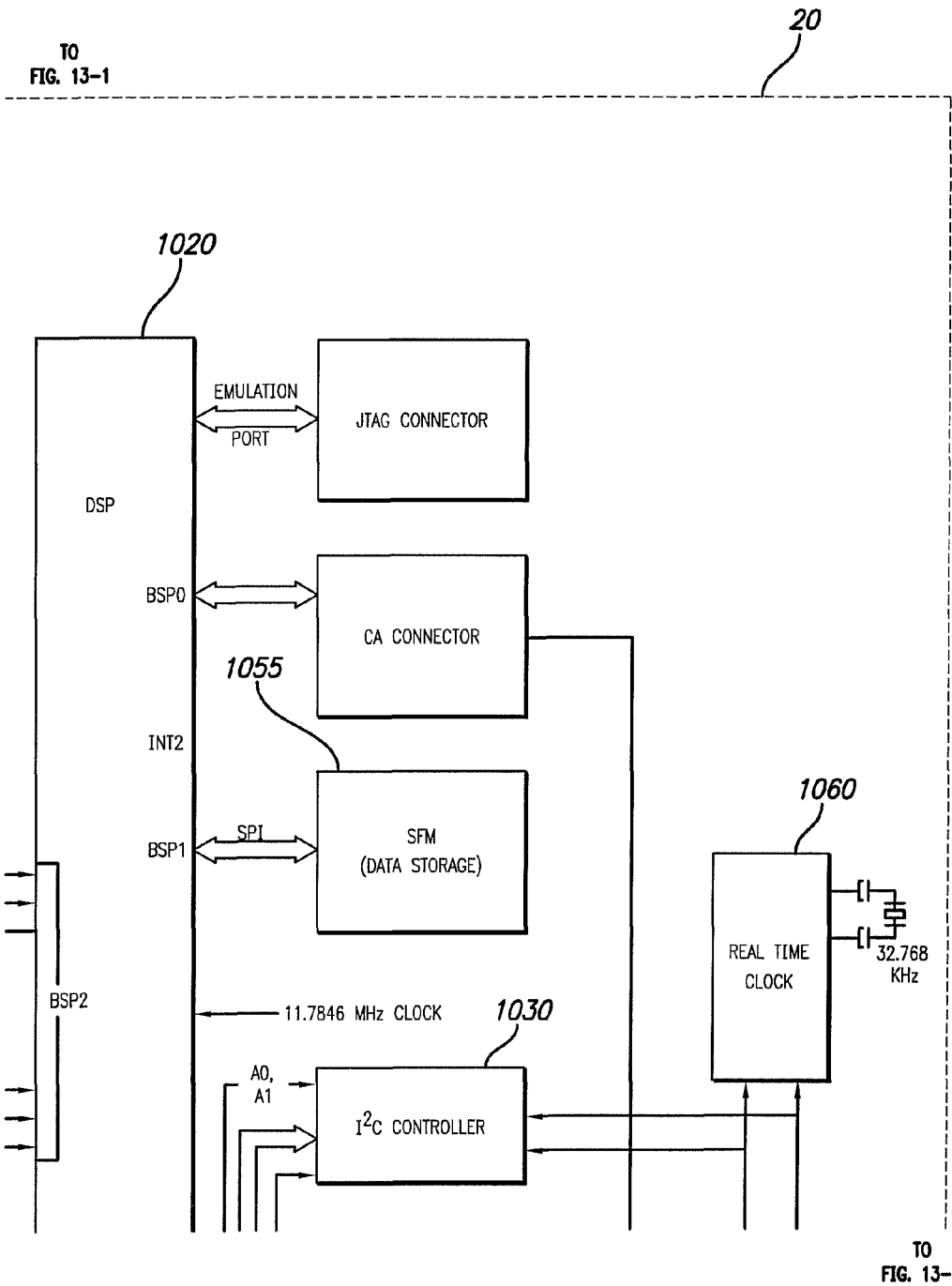
Figures 3, 13:
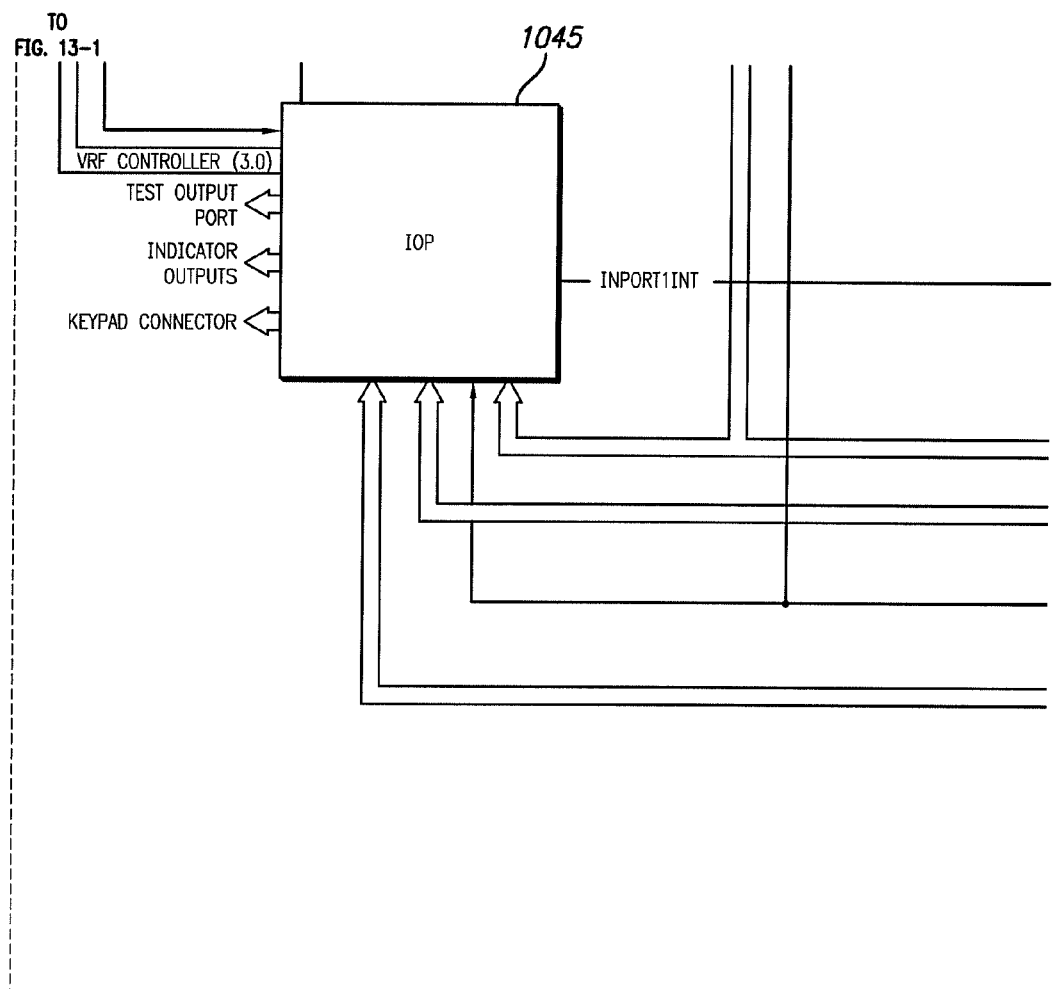
Figures 4, 13:
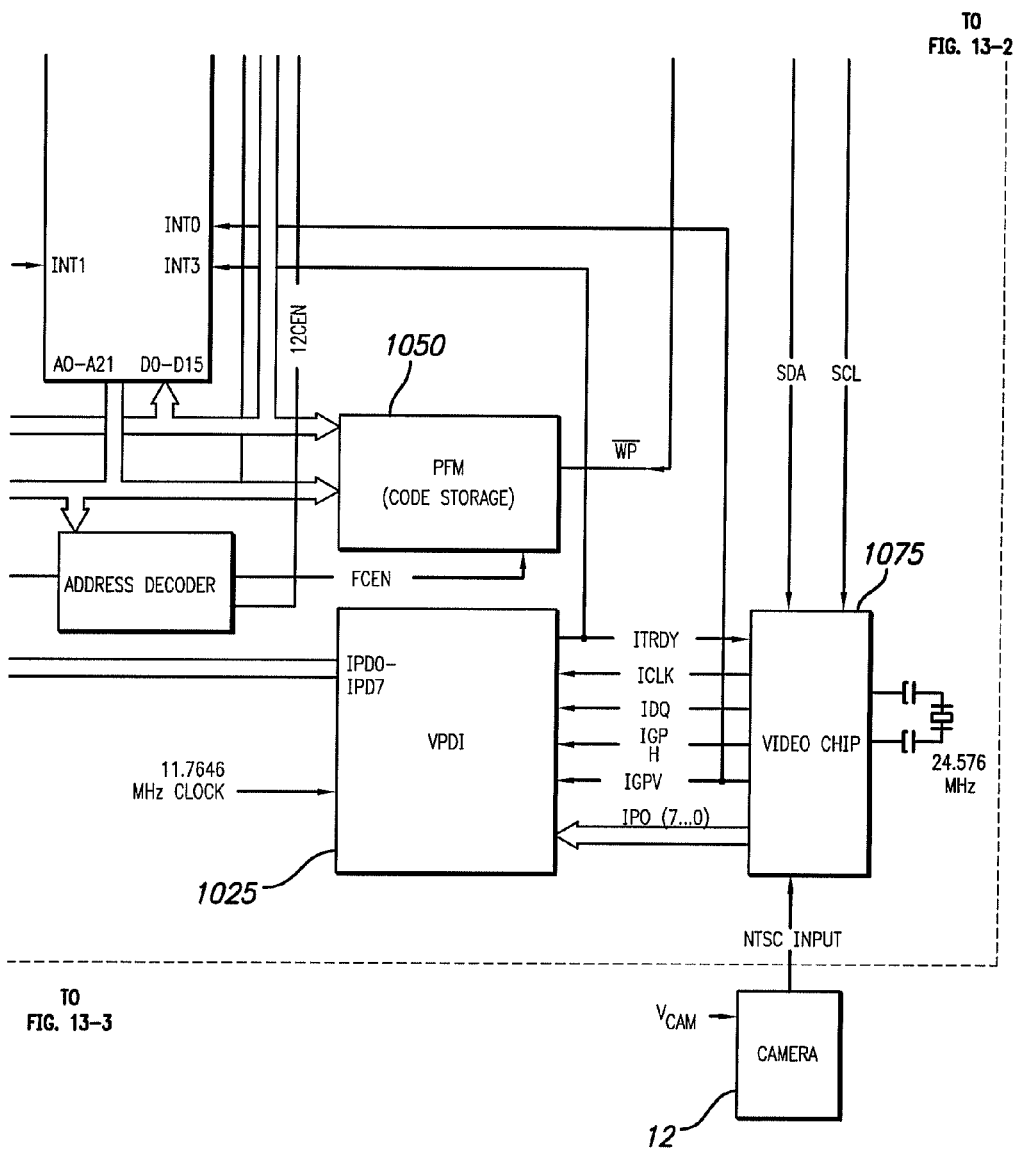

One exemplary embodiment of the VPU 20 is shown in FIG. 13. The VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I$^2$C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 20. The Power Supply, Distribution and Motoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 12 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I$^2$C Protocol Controller 1030 may serve as a link between the DSP 1020 and the I$^2$C bus. The I$^2$C Protocol Controller 1030 may be able to convert the parallel bus interface of the DSP 1020 to the I$^2$C protocol bus or vise versa. The I$^2$C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR and BCLKR for the DSP 1020. The Input/Output Ports 1045 provide expanded 10 functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system 1.

It is known that neurons respond best to change in stimuli. The retina, if continuously stimulated in a consistent manner, will slowly become less and less sensitive to the stimulus. This causes the perception of a constant visual image to gradually disappear. Those with normal vision are unable to perceive this effect because the eye constantly moves through motions called jitter or microsaccades. A normal retina has a resolution of approximately four million light transducer cells (rods and cones), hence it requires a minute movement to change the light intensity cast upon a given light transducer.

Known retinal prostheses have two disadvantages. First, the resolution of an electrode array applied to the retina of known prostheses is significantly lower than the resolution of a healthy retina, thus requiring a greater movement of the eye to move an image from one electrode to the next electrode, as compared to one cone to the next cone. Second, a head mounted camera of a known prosthesis does not have the natural jitter or microsaccades of an actual eye. These disadvantages may be overcome by introducing jitter at the level of the image (captured by the camera 12), or introduce jitter at the level of the stimulation pulses (in a spatio-temporal fashion).

It is also known that some neural processing is done within the retina. Hence, a continuously stimulated cone will not result in a continuous signal to the brain. Ganglion and bipolar cells pass along this change in information more readily than constant information. In a diseased retina, rods and cones cannot be stimulated, since they are dead. Electrically stimulating cells further along the neural pathway, bypasses some of the neural processing. This neural processing may be simulated electronically to gain normal brain stimulation. In one exemplary embodiment, the neural processing may be implement with custom image processing algorithms motivated by retinal processing, like the Difference of Gaussian filter that may be use in the VPU 20's firmware to pre-process the image.

When implanting the electrode array 2 of the Retinal stimulation system 1, it may be best to implant the electrode array 2 close to the retina without crushing it. To make sure that the electrode array 2 is at least in contact with the retina, it is possible to measure the impedance of the electrodes as the electrode array 2 is being implanted into the patient's eye. Saline vitreous of the eye is more conductive than retinal tissue. Therefore, high impedance in the electrodes of the electrode array 2 means good retinal tissue contact and that requires less electrical stimulation of the retina to create the perception of a pixel of light in the subject's eye. However, low impedance in the electrodes of the electrode array 2 means poor retinal tissue contact and that requires more electrical stimulation of the retina to create the perception of a pixel of light in the subject's eye. In one exemplary embodiment, the electrical stimulation of the retina to create the perception of a pixel of light in the subject's eye may be performed by applying less current to electrodes in the electrodes of the array 2 of FIG. 2 that have higher impedance (i.e. the electrodes are contacting the retina). Applying less current to the electrodes may result in better focal percepts, may effectively increase the dynamic range if percepts are generated at low currents, may result in longer lifetime of the electrodes, and less damage to the tissue underneath the electrodes.

In one embodiment, the graphical user interface of the Fitting System (FS) shown in FIG. 9 may be used to determine the impedance of each electrode in the electrode array 2 of FIG. 2 after the electrode array 2 has been implanted in the subject's eye.

Figure 14:
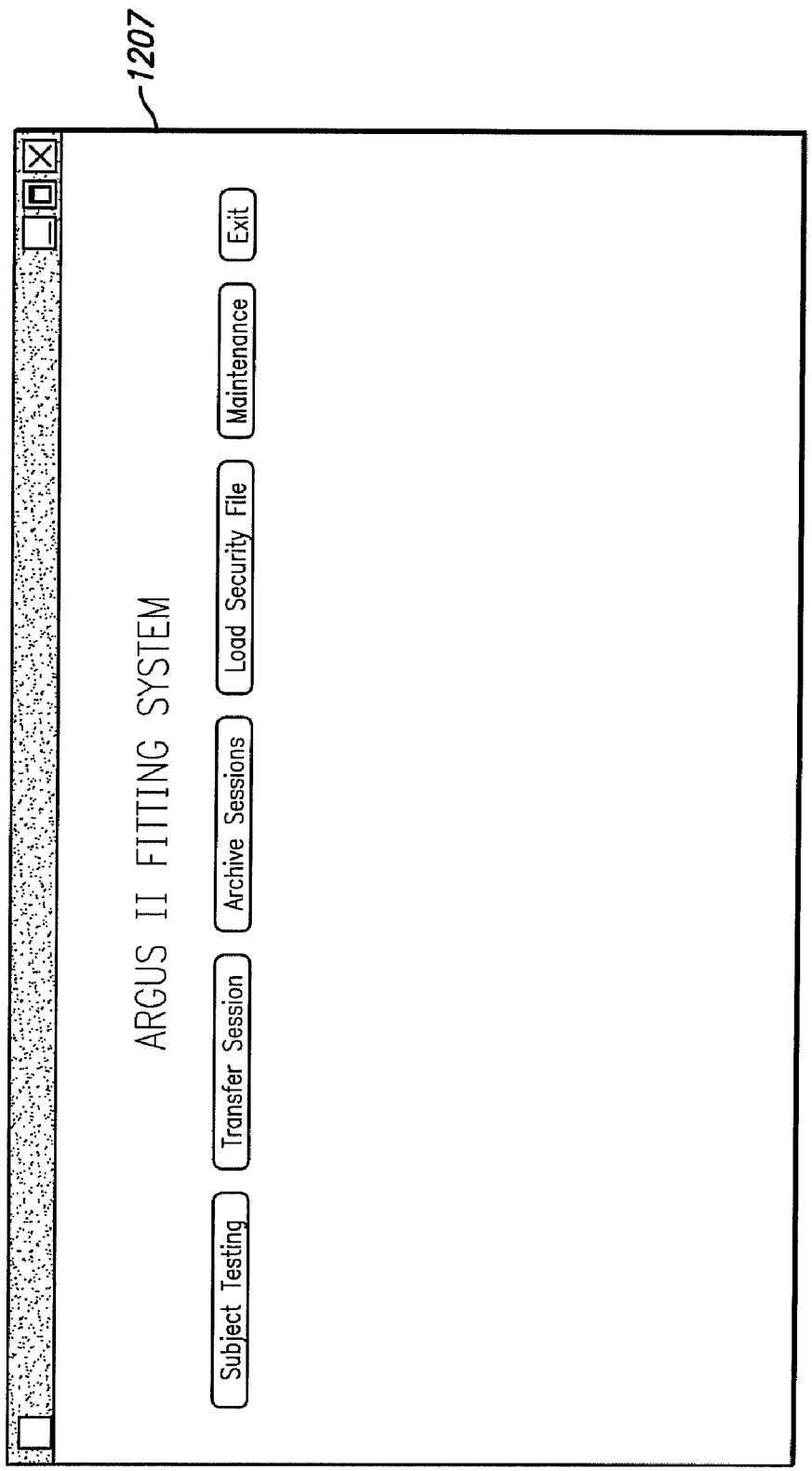
FIG. 14 shows a Main Menu computer screen.

The graphical user interface of the Fitting System shown in FIG. 9 may have six options on the FS Main Menu 1207 as shown in FIG. 14. For example, Subject Testing, Transfer Session, Archive Sessions, Load Security File, Maintenance, and Exit.

The Subject Testing option may be selected when performing: diagnostic check (i.e. impedance and waveforms) on the status of the implant, viewing waveforms for selected electrodes, loading a video configuration file to the VPU 20 and stimulating the subject using the downloaded video stimulation parameters, executing psychophysical experiments. The Transfer Session option may be selected when copying file(s) to a thumb drive. The Archive Sessions option may be selected when archiving all data files on the FS laptop 10 of FIG. 9 to the external drive 49 of FIG. 9. The Load Security File option may be selected to enable use of the Fitting System. The Load Security File option may be chosen at the initial clinical testing session. The Maintenance option may be selected to perform maintenance on one or more components of the system. The Maintenance option may be set up to only be accessed by an authorized person. The Exit option may be selected to close out the main menu.

The Subject Testing option is more fully described in the following paragraphs.

Prior to using the Subject Testing option, the VPU 20 shown in FIGS. 11-12 should be on, the subject should put on the visor/Glasses 5, the Glasses 5 should be adjusted until a link is obtained with the implant, and the VPU 20 should confirm that the implant is working by running start-up tests.

Figure 15:
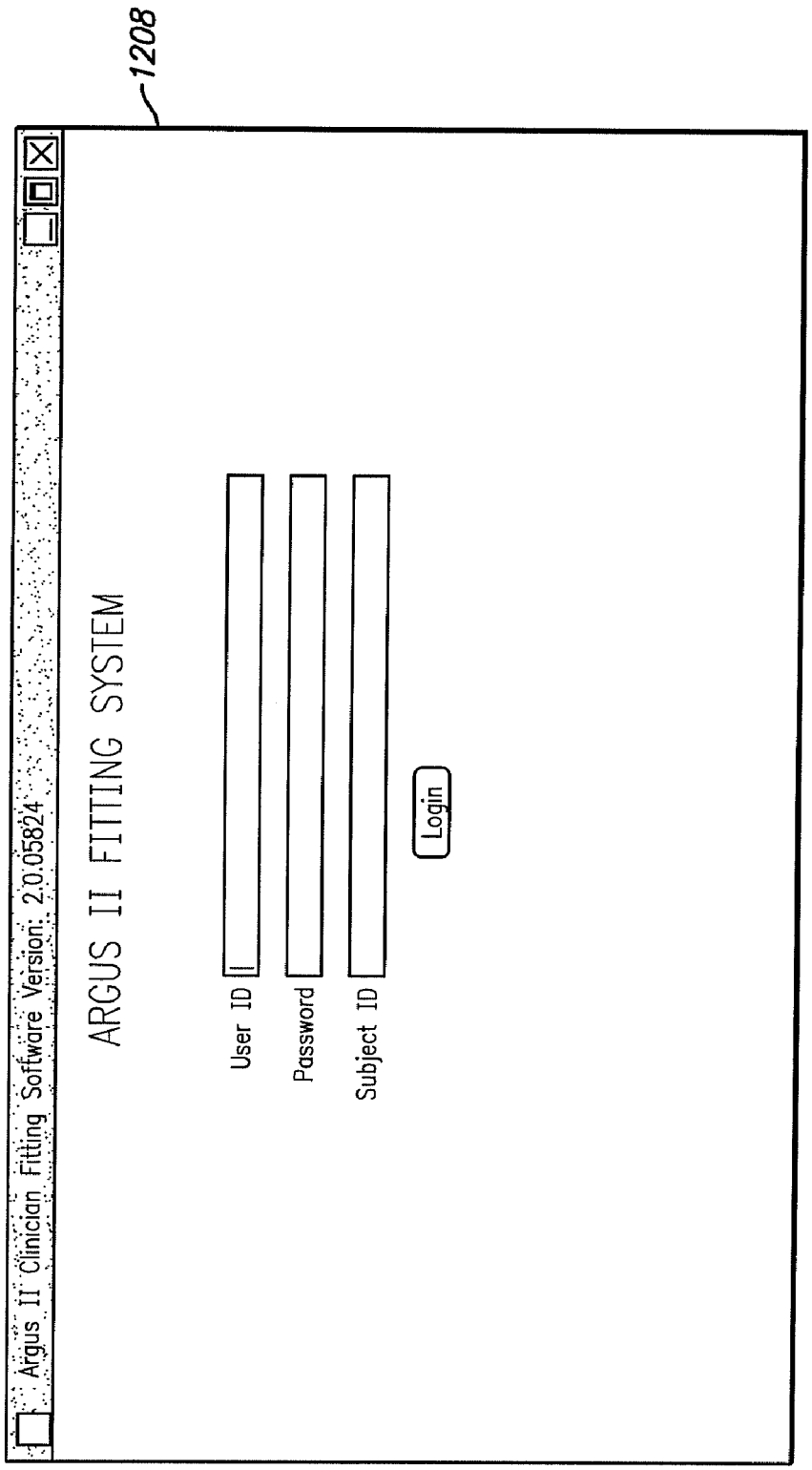
FIG. 15 shows a Login computer screen.

Once the Subject Testing option is selected from window 1207, a login screen 1208 shown in FIG. 15 may be displayed with fields for User ID, Password and Subject ID. After the login, a diagnostic application may be initiated to display the status of the implant. Through the diagnostic application, an electrode integrity check may be performed and the electrode status may be displayed and the impedance and waveforms for each of the electrodes can be measured.

Figure 16:
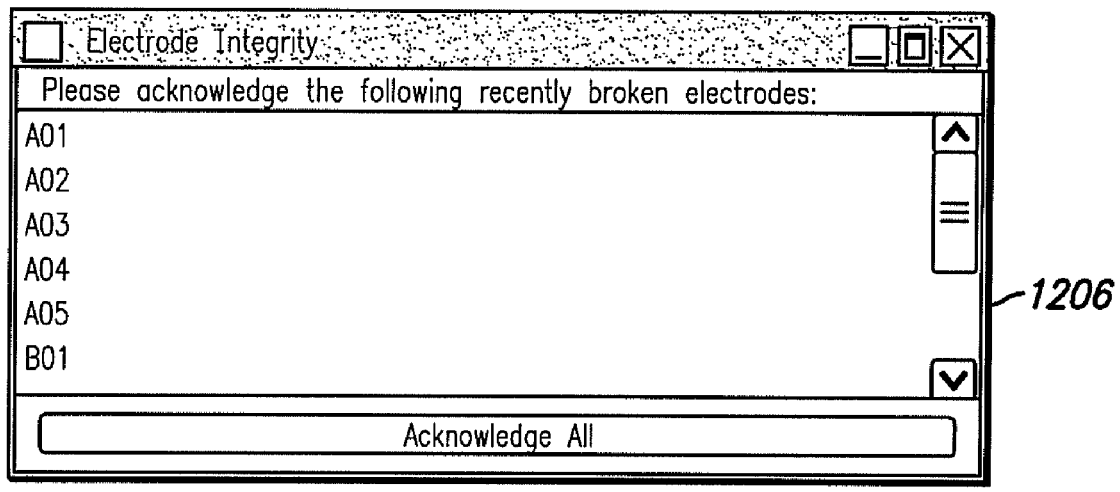
FIG. 16 shows an 'Electrode Integrity' message box.

An "Electrode Integrity" message box 1206, shown in FIG. 16, may be displayed in the event that any newly broken/shorted electrodes are detected or broken/shorted electrodes are present. If no newly detected broken/shorted electrodes are detected, this message box will not appear and the diagnostics screen 1209 shown in FIG. 17 may be displayed.

Figure 17:
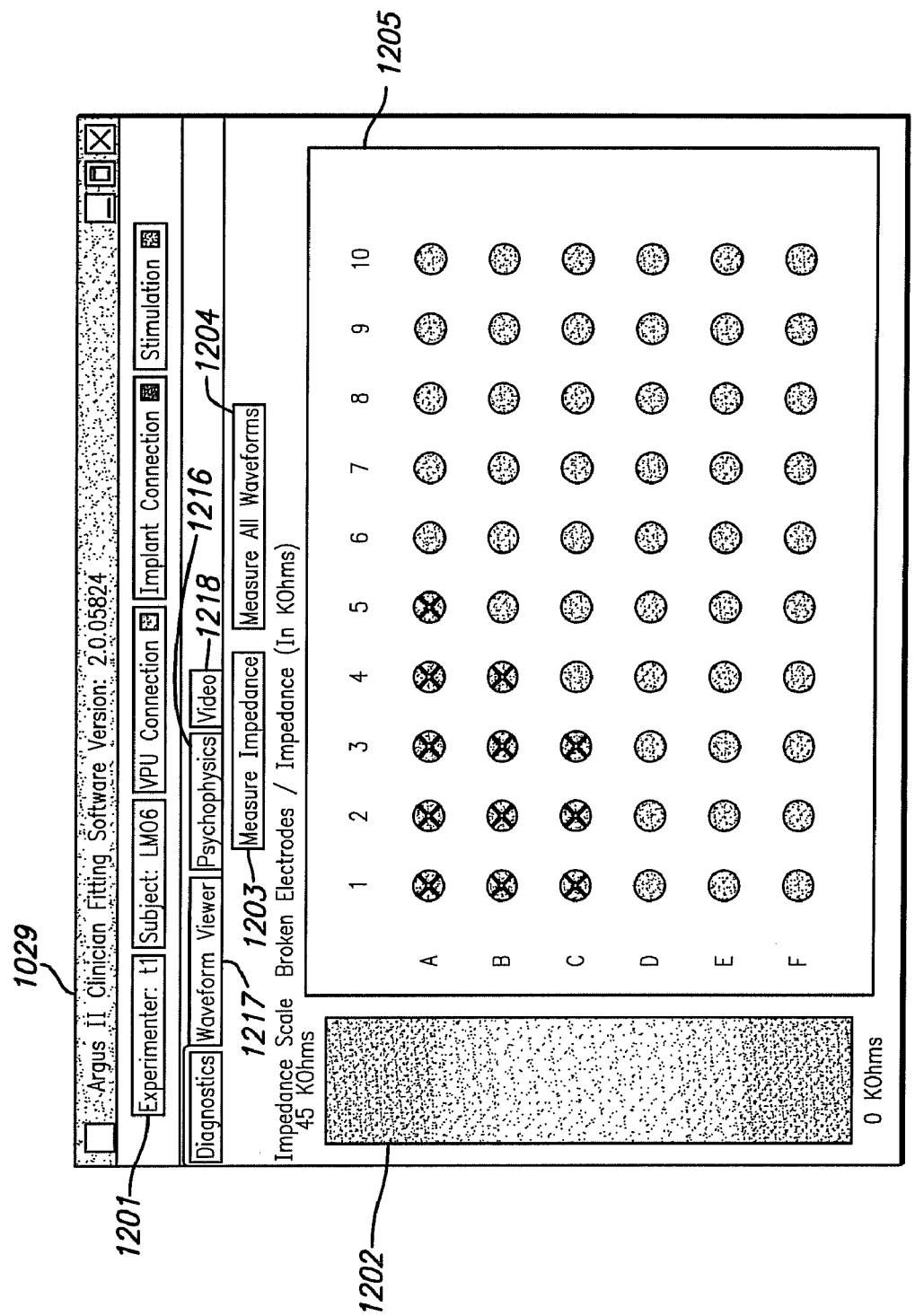
FIG. 17 shows a diagnostics computer screen.

The Diagnostic Module Screen 1209 shown in FIG. 17 may contain: 1) Session Information 1201 displaying (a) Experimenter (User) ID, (b) Subject ID, (c) VPU Connection identifying the status of the connection of the VPU 20 to the FS, (d) Implant Connection identifying the status of the connection of the implant to the FS, and (e) Stimulation identifying the status of stimulation (i.e., whether or not stimulation is occurring); 2) Measure Impedance 1203 for measuring impedance for the electrodes; 3) Measure All Waveforms 1204 for measuring waveforms for the electrodes; 4) Broken Electrodes/Impedance (in kOhms)—6×10 Electrode Grid 1205 representing each of the implant electrodes. The view of the electrodes is from the perspective of the subject. The electrodes shown as "(x)" are designated as broken/shorted or are designated as being deselected from being tested. When measuring impedance, the values will appear directly under each represented electrode. Stimulation should not occur on electrodes designated as broken; and 5) Impedance Scale 1202 for impedance that ranges from 0 to 45 kOhms.

Figure 18:
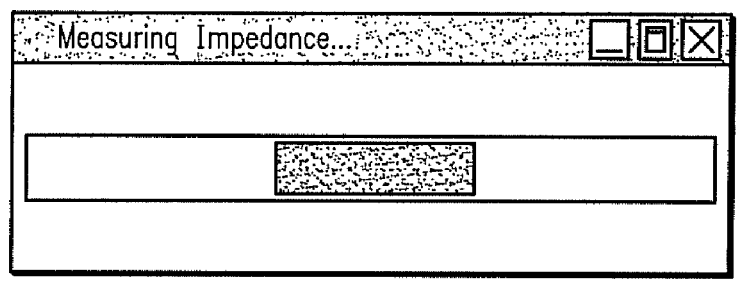
FIG. 18 shows a 'Measuring Impedance' message box.
Figure 19:
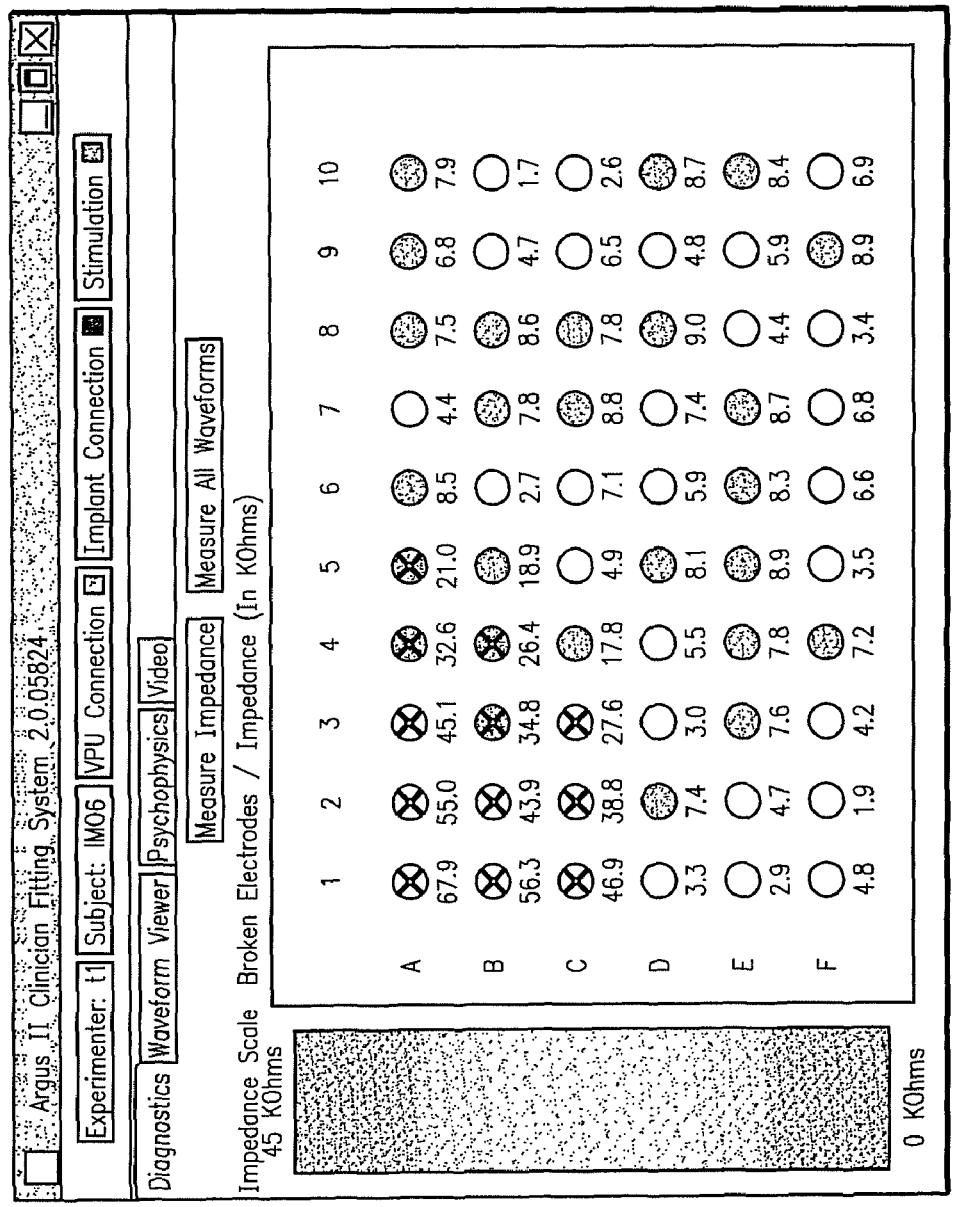
FIG. 19 shows a computer screen indicating impedance values.

Clicking on the Measure Impedance 1203 of FIG. 17 will measure impedance of the electrodes and a message box shown in FIG. 18 may be used to indicate the progress of obtaining impedance measurements. Once the impedance measurements are completed, the impedance values (in kOhms) will be displayed as shown in FIG. 19 under each represented electrode. Each of the electrodes may be color coded based on where the impedance value falls within the impedance scale from 0 to 45 kOhms of the Impedance Scale 1202. The impedance values for the subject may be automatically stored in a file marked for transfer on the FS laptop 10.

In one exemplary embodiment, it may be advantageous to provide a surgeon with real time impedance information about the electrodes in the electrode array 2 of FIG. 2 during surgery to aid the surgeon in placing the electrode array 2 close to the retina without crushing it.

In one embodiment, the Diagnostic Module Screen 1209 shown in FIG. 17 may be used to determine the impedance of each electrode in the electrode array 2 while the electrode array 2 is being implanted in the subject's eye. The retinal stimulation system 1 of FIG. 2 provides bidirectional data through an RF link between the external coil 14 and internal coil 116. During the surgery, stimulation information may be provided to the retinal stimulation system 1 of FIG. 2 and telemetry including voltage drop, from which impedance is calculated, is sent back. Impedance measurement may be conducted with sub-threshold stimulation current. A sub-threshold stimulation is a current that is too small to create a percept. The sub-threshold stimulation current may still return a voltage drop measurement that can be used to calculate impedance using Ohm's law: R=voltage drop/stimulation current.

After the impedance of electrodes in the electrode array 2 of FIG. 2 has been measured, the physician/surgeon can quickly scan the Diagnostic Module Screen 1209 of FIG. 17 to assess the placement or any areas that are working better than others. This allows the surgeon to quickly assess multiple locations. To fine tune the location, it may be advantageous to measure impedance at multiple frequencies. This may be activated by a "measure all waveforms" button 1204, also shown in FIG. 17.

To measure waveforms, Clicking on "Measure All Waveforms" 1204 will measure waveforms of the electrodes. Once the measurements are complete, the waveform information may be stored in a file marked for transfer on the FS laptop 10. The waveforms for each of the electrodes can be viewed from the Waveform Viewer 1217 shown in FIG. 20.

Figure 20:
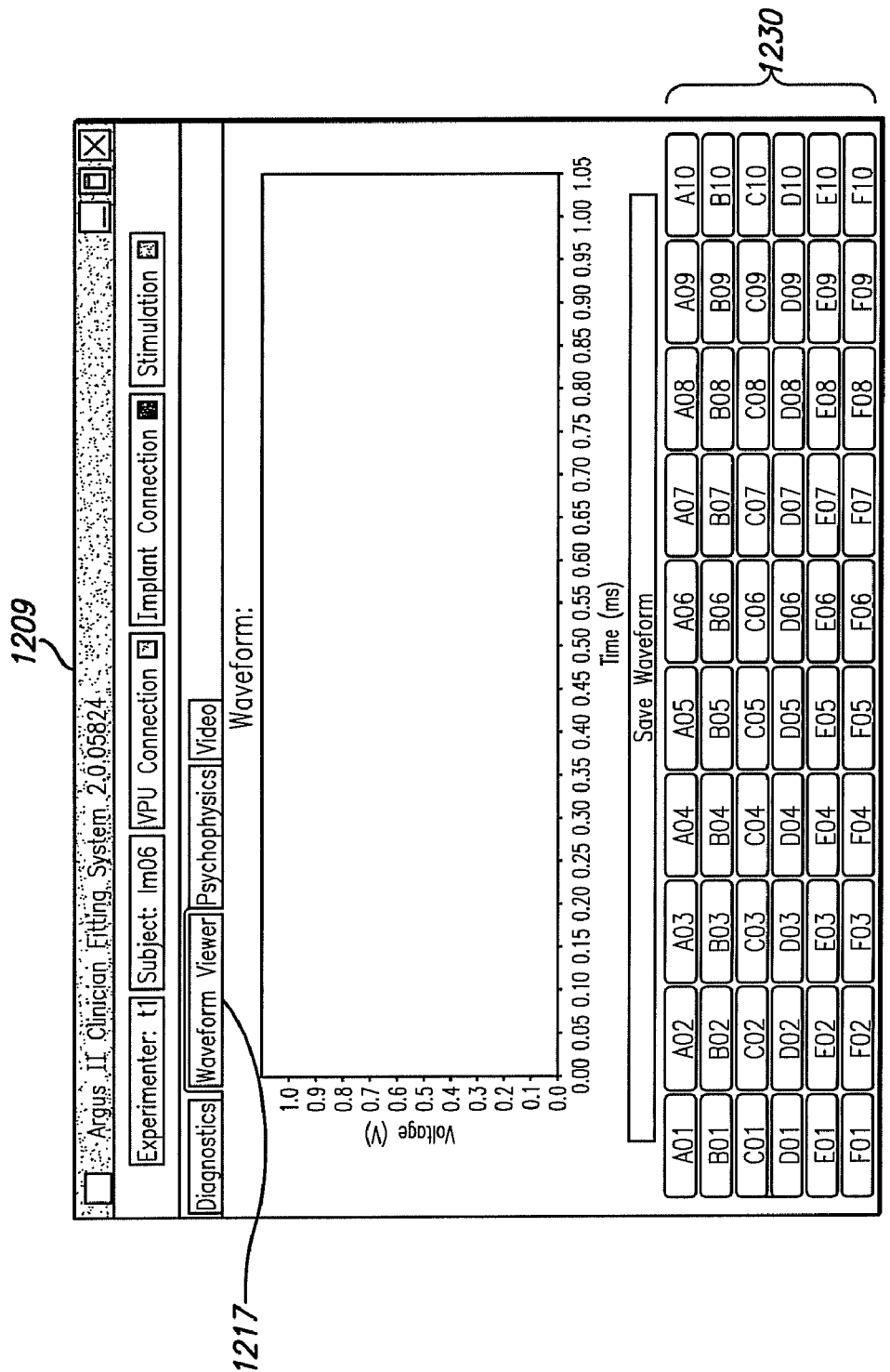
FIGS. 20 and 21 show waveform computer screens.
Figure 21:
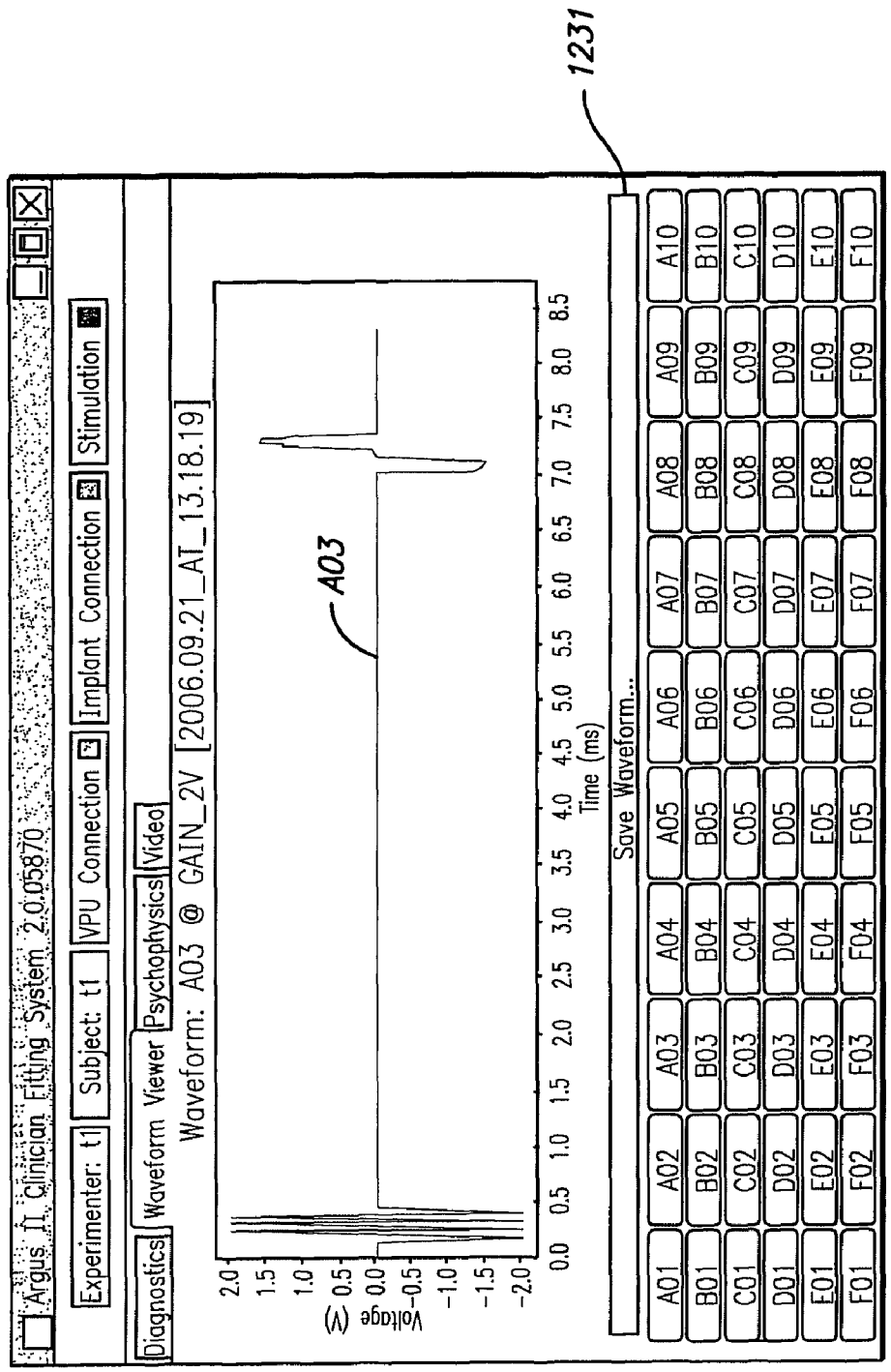

The Waveform Viewer 1217 shown in FIG. 20 is a utility that may be used to measure and view the waveform of a selected electrode. From the list of the electrodes at the bottom of the screen (displayed in a 6×10 configuration 1230 with their Cartesian coordinates), a specific electrode for which to measure the waveform may be selected. Upon selection of the electrode, the VPU 20 will record the waveform and the information will be sent to the FS so that the waveform data may be presented on the screen as shown in FIG. 21 in which, for example, the waveform of electrode A03 is measured during stimulation. By right-clicking on the mouse, it may be possible to zoom in and zoom out on the displayed waveform. The waveform may be saved by clicking on the "Save Waveform" button 1231.

Figure 22:
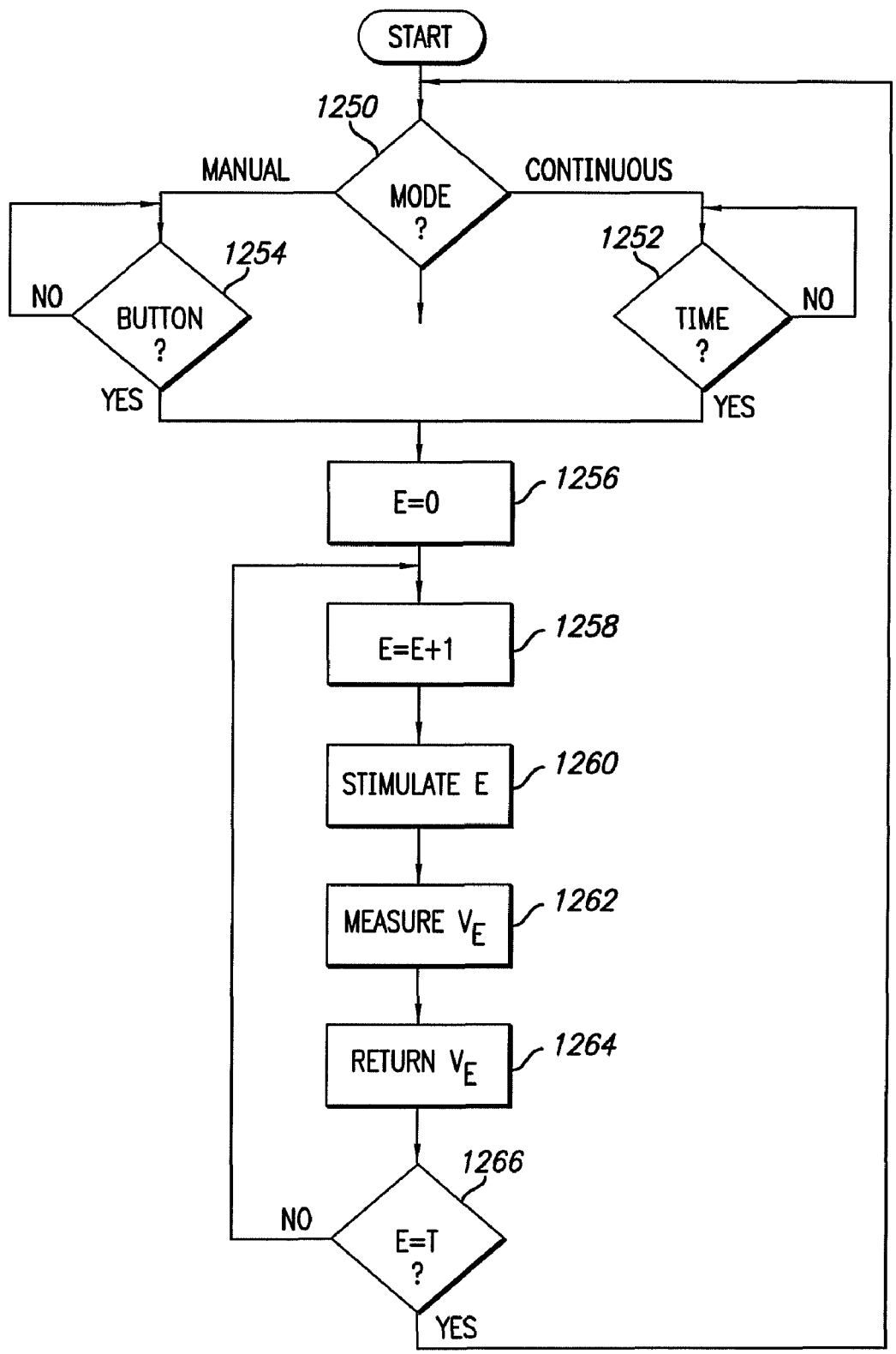
FIG. 22 shows flow chart of the testing procedure.

The impedance measurement may be continuous or activated manually by a measure impedance button 1203, see FIG. 17, as already discussed before. FIG. 22 is a flow chart of an embodiment of the testing procedure. Referring to FIG. 22, the testing software first determines if the impedance measurement is to be done continuously (output "Continuous" of step 1250) or is to be done manually (output "Manual" of step 1250). In continuous mode, the software may continuously test a timer (not shown) for the next testing event. "Continuous" may mean that the timer is tested at a set time interval, for example, every millisecond. If it is time for the next test (output "Yes" of step 1252), the software proceeds to step 1256. If it is not time for the next test (output "No" of step 1252), the software continues to test the timer. In manual☐mode, the software tests for depression of test button 1203. If test button 1203 is not depressed (output "No" of step 1254), the software continues to wait. If test button 1203 is depressed (output "Yes" of step 1254), the software proceeds to step 1256.

First, the electrode counter "E" is set to 0 in step 1256, and incremented by one in step 1258. The electrode with the number corresponding to the value of the counter "E" is stimulated in step 1260 with, for example, a sub-threshold stimulation pulse. The voltage value $V_E$ (or voltage difference corresponding to $V_E$) is measured in step 1262 and the value $V_E$ is returned, for example, to the VPU 20 in step 1264. If the value of the counter "E" is not equal to the total number of electrodes (output "No" of step 1266), the process is repeated until the condition E=T is reached, meaning that all electrodes have been measured. Upon measuring all electrodes (output "Yes" of step 1266), the software returns to check the mode in step 1250.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Accordingly, what has been shown is an improved visual prosthesis, improved method of stimulating a subject's retina and an improved method for implanting electrodes in a subject's retina. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein. Although the above disclosure pertains to visual prosthesis and a subject's eye, it should also be understood that this disclosure may also pertain to other areas, like, for example, semiconductors.

What is claimed is:

1. A method for providing visual impedance feedback when implanting electrodes in a subject's retina, the method comprising:
   a) determining a maximum effective impedance;
   b) temporarily placing an two dimensional array of electrodes in a subject's retina;
   c) determining impedance of the placed electrodes;
   d) monitoring impedance of the electrodes, not exceeding the maximum effective impedance, using a visual interface, the visual interface including a two dimensional grid corresponding to the two dimensional array of electrodes displaying numerical impedance values for the electrodes, and providing for manual adjustment of current on each electrode;
   e) moving the array of electrodes;
   f) repeating features a) through d) until impedance of the electrodes is ideal for permanent implanting of the electrodes; and
   g) permanently implanting the array of electrodes on the retina.

2. The method of claim 1, wherein the array of electrodes is an array of 6×10 electrodes.

3. The method of claim 1, wherein determining impedance of the electrodes comprises:
   applying current through the electrodes;
   determining voltage drop across each of the electrodes; and
   calculating impedance of each electrode based on the voltage drop across each electrode.

4. The method of claim 3, wherein the current applied to the electrodes when determining the impedance of the electrodes is below a threshold current required to create perception of light by the subject.

5. A method to provide visual impedance feedback when determining which electrode is to be in contact with a subject's retina, the method comprising:
   determining an maximum effective impedance;
   applying current to a two dimensional array of electrodes implanted in the subject's eye;
   determining impedance of each electrode of the two dimensional array of electrodes;
   providing a visual user interface configured to show numerical impedance values of the electrodes in a two dimensional grid corresponding to the two dimensional array of electrodes;

establishing the electrode with the highest impedance, not exceeding the maximum effective impedance, as the electrode in contact with the subject's retina and providing for manual adjustment of electrode current through the visual user interface.

6. The method of claim 5, wherein the array of electrodes is an array of 6×10 electrodes.

7. The method of claim 5, wherein determining impedance of each electrode comprises:

determining voltage drop across each of the electrodes; and calculating impedance of each electrode based on the voltage drop across each electrode.

8. The method of claim 5, wherein the current being applied to the electrodes is below a threshold current required to create perception of light by the subject.

* * * * *